US011622919B2

(12) United States Patent
Knowlson et al.

(10) Patent No.: US 11,622,919 B2
(45) Date of Patent: Apr. 11, 2023

(54) HYDROENTANGLED AIRLAID WEB AND PRODUCTS OBTAINED THEREFROM

(71) Applicant: Jacob Holm & Sons AG, Candler, NC (US)

(72) Inventors: Richard Knowlson, Charlotte, NC (US); Eric Mariani, Richwiller (FR); Katherine Dyrmose Petersen, Thann (FR)

(73) Assignee: Jacob Holm & Sons AG, Candler, NC (US)

( * ) Notice: Subject to any disclaimer, the term of this patent is extended or adjusted under 35 U.S.C. 154(b) by 0 days.

(21) Appl. No.: 15/099,911

(22) Filed: Apr. 15, 2016

(65) Prior Publication Data

US 2016/0228337 A1 Aug. 11, 2016

Related U.S. Application Data

(62) Division of application No. 13/943,146, filed on Jul. 16, 2013, now Pat. No. 9,394,637.

(Continued)

(51) Int. Cl.
*A61K 8/02* (2006.01)
*D04H 1/425* (2012.01)
(Continued)

(52) U.S. Cl.
CPC ............ *A61K 8/0208* (2013.01); *B08B 1/006* (2013.01); *D04H 1/425* (2013.01); *D04H 1/46* (2013.01);
(Continued)

(58) Field of Classification Search
CPC .......... D04H 1/425; D04H 1/46; D04H 1/492; D04H 1/495
See application file for complete search history.

(56) References Cited

U.S. PATENT DOCUMENTS 2,862,251 A 12/1958 Kalwaites
3,508,308 A 4/1970 Bunting Jr. et al.
(Continued)

FOREIGN PATENT DOCUMENTS

CN 101517140 A 8/2009
EP 0 303 528 A1 2/1989
(Continued)

OTHER PUBLICATIONS

Office Action dated Jul. 27, 2016 in Australian Patent Application No. 2013360337.
(Continued)

*Primary Examiner* — Marla D McConnell
*Assistant Examiner* — Kevin Worrell
(74) *Attorney, Agent, or Firm* — Oblon, McClelland, Maier & Neustadt, L.L.P.

(57) ABSTRACT

A water disposable nonwoven web having good MD and CD strength is provided. The nonwoven web is obtained by hydroentangling an airlaid web of no less than 50% by weight of natural cellulose fibers having a fiber length of no more than 3.5 mm and no more than 50% by weight staple fibers having a fiber length of no less than 8.0 mm. The nonwoven web contains no adhesive, binder or thermal bonding fibers. Products containing the disposable nonwoven web meet municipal guidelines for flushability.

4 Claims, 3 Drawing Sheets

Related U.S. Application Data

(60) Provisional application No. 61/736,837, filed on Dec. 13, 2012.

(51) Int. Cl.

*D04H 1/492* (2012.01)
  *D04H 1/46* (2012.01)
  *B08B 1/00* (2006.01)
  *D04H 5/03* (2012.01)

(52) U.S. Cl.
  CPC .............. *D04H 1/492* (2013.01); *D04H 5/03* (2013.01); *D10B 2201/01* (2013.01); *D10B 2509/026* (2013.01)

(56) References Cited

U.S. PATENT DOCUMENTS

| | | |
|---|---|---|
| 3,949,035 A | 4/1976 | Dunning et al. |
| 4,252,761 A | 2/1981 | Schoggen et al. |
| 4,321,924 A | 3/1982 | Ahr |
| 4,323,069 A | 4/1982 | Ahr et al. |
| 4,324,246 A | 4/1982 | Mullane et al. |
| 4,327,729 A | 5/1982 | King |
| 4,362,781 A | 12/1982 | Anderson |
| 4,425,130 A | 1/1984 | DesMarais |
| 4,452,837 A | 6/1984 | Clausen et al. |
| 4,475,911 A | 10/1984 | Gellert |
| 4,551,191 A | 11/1985 | Kock et al. |
| 4,640,810 A | 2/1987 | Laursen et al. |
| 4,755,421 A | 7/1988 | Manning et al. |
| 4,801,482 A | 1/1989 | Goggans et al. |
| 4,869,855 A | 9/1989 | Twilley et al. |
| 4,950,531 A | 8/1990 | Radwanski et al. |
| 5,026,591 A | 6/1991 | Henn et al. |
| 5,035,941 A | 7/1991 | Blackburn |
| 5,066,527 A | 11/1991 | Newell |
| 5,074,854 A | 12/1991 | Davis |
| 5,093,190 A | 3/1992 | Kwok et al. |
| 5,226,991 A | 7/1993 | Svaighert |
| 5,227,228 A | 7/1993 | Newell |
| 5,254,399 A | 10/1993 | Oku et al. |
| 5,292,581 A | 3/1994 | Viazmensky et al. |
| 5,295,986 A | 3/1994 | Zehner et al. |
| 5,295,997 A | 3/1994 | Vuillaume et al. |
| 5,308,673 A | 5/1994 | Tochacek et al. |
| 5,310,590 A | 5/1994 | Tochacek et al. |
| 5,320,900 A | 6/1994 | Oathout |
| 5,353,485 A | 10/1994 | Billgren et al. |
| 5,366,453 A | 11/1994 | Zehner et al. |
| 5,368,668 A | 11/1994 | Tochacek et al. |
| 5,383,616 A | 1/1995 | Svaighert |
| 5,387,208 A | 2/1995 | Ashton et al. |
| 5,389,202 A | 2/1995 | Everhart et al. |
| 5,393,304 A | 2/1995 | Vuillaume et al. |
| 5,393,599 A | 2/1995 | Quantrille et al. |
| 5,405,342 A | 4/1995 | Roessler et al. |
| 5,425,725 A | 6/1995 | Tanzer et al. |
| 5,451,219 A | 9/1995 | Suzuki et al. |
| 5,458,591 A | 10/1995 | Roessler et al. |
| 5,459,912 A | 10/1995 | Oathout |
| 5,460,622 A | 10/1995 | Dragoo et al. |
| 5,476,457 A | 12/1995 | Roessler et al. |
| 5,486,167 A | 1/1996 | Dragoo et al. |
| 5,489,282 A | 2/1996 | Zehner et al. |
| 5,492,753 A | 2/1996 | Levy et al. |
| 5,506,041 A | 4/1996 | Tanaka et al. |
| 5,509,913 A | 4/1996 | Yeo |
| 5,527,300 A | 6/1996 | Sauer |
| 5,540,672 A | 7/1996 | Roessler et al. |
| 5,542,566 A | 8/1996 | Glaug et al. |
| 5,543,004 A | 8/1996 | Tochacek et al. |
| 5,549,592 A | 8/1996 | Fries et al. |
| 5,558,655 A | 9/1996 | Jezzi et al. |
| 5,562,645 A | 10/1996 | Tanzer et al. |
| 5,562,646 A | 10/1996 | Goldman et al. |
| 5,562,650 A | 10/1996 | Everett et al. |
| 5,578,344 A | 11/1996 | Ahr et al. |
| 5,582,903 A | 12/1996 | Levy et al. |
| 5,591,149 A | 1/1997 | Cree et al. |
| 5,593,399 A | 1/1997 | Tanzer et al. |
| 5,599,335 A | 2/1997 | Goldman et al. |
| 5,599,550 A | 2/1997 | Kohlruss et al. |
| 5,599,585 A | 2/1997 | Cohen |
| 5,607,551 A | 3/1997 | Farrington, Jr. et al. |
| 5,609,707 A | 3/1997 | Bazshushtari et al. |
| 5,609,809 A | 3/1997 | Tanaka et al. |
| 5,611,790 A | 3/1997 | Osborn, III et al. |
| 5,613,959 A | 3/1997 | Roessler et al. |
| 5,614,298 A | 3/1997 | Tanaka et al. |
| 5,616,201 A | 4/1997 | Finch et al. |
| 5,620,694 A | 4/1997 | Girardot |
| 5,624,729 A | 4/1997 | Cohen et al. |
| 5,629,081 A | 5/1997 | Richards et al. |
| 5,638,569 A | 6/1997 | Newell |
| 5,649,336 A | 7/1997 | Finch et al. |
| 5,649,919 A | 7/1997 | Roessler et al. |
| 5,656,132 A | 8/1997 | Farrington, Jr. et al. |
| 5,658,269 A | 8/1997 | Osborn, III et al. |
| 5,667,635 A | 9/1997 | Win et al. |
| 5,669,894 A | 9/1997 | Goldman et al. |
| 5,670,110 A | 9/1997 | Dirk et al. |
| 5,674,212 A | 10/1997 | Osborn, III et al. |
| 5,681,300 A | 10/1997 | Ahr et al. |
| 5,683,375 A | 11/1997 | Osborn, III et al. |
| 5,688,588 A | 11/1997 | Cotton et al. |
| 5,695,486 A | 12/1997 | Broughton et al. |
| 5,702,382 A | 12/1997 | Osborn, III et al. |
| 5,713,884 A | 2/1998 | Osborn, III et al. |
| 5,716,703 A | 2/1998 | Payne |
| 5,720,851 A | 2/1998 | Reiner |
| 5,722,966 A | 3/1998 | Christon et al. |
| 5,733,635 A | 3/1998 | Terakawa et al. |
| 5,744,149 A | 4/1998 | Girardot |
| 5,749,863 A | 5/1998 | Payne |
| 5,756,112 A | 5/1998 | Mackey |
| 5,763,044 A | 6/1998 | Ahr et al. |
| 5,763,332 A | 6/1998 | Gordon et al. |
| 5,765,717 A | 6/1998 | Gottselig |
| 5,772,845 A | 6/1998 | Farrington, Jr. et al. |
| 5,824,004 A | 10/1998 | Osborn, III et al. |
| 5,827,259 A | 10/1998 | Laux et al. |
| 5,833,678 A | 11/1998 | Ashton et al. |
| 5,843,058 A | 12/1998 | Quist |
| 5,849,816 A | 12/1998 | Suskind et al. |
| 5,853,538 A | 12/1998 | Reiner |
| 5,858,011 A | 1/1999 | Brown et al. |
| 5,863,663 A | 1/1999 | Mackey et al. |
| 5,869,411 A | 2/1999 | Bazshushtari et al. |
| 5,876,391 A | 3/1999 | Roe et al. |
| 5,879,779 A | 3/1999 | Zafiroglu |
| 5,882,769 A | 3/1999 | McCormack et al. |
| 5,895,380 A | 4/1999 | Turi et al. |
| 5,904,673 A | 5/1999 | Roe et al. |
| 5,904,675 A | 5/1999 | Laux et al. |
| 5,910,455 A | 6/1999 | Maddern et al. |
| 5,916,678 A | 6/1999 | Jackson et al. |
| 5,932,068 A | 8/1999 | Farrington, Jr. et al. |
| 5,935,880 A | 8/1999 | Wang et al. |
| 5,947,945 A | 9/1999 | Cree et al. |
| 5,948,540 A | 9/1999 | Mackey et al. |
| 5,948,710 A | 9/1999 | Pomplun et al. |
| 5,951,536 A | 9/1999 | Osborn, III et al. |
| 5,952,043 A | 9/1999 | Mackey et al. |
| 5,952,251 A | 9/1999 | Jackson et al. |
| 5,957,909 A | 9/1999 | Hammons et al. |
| 5,958,186 A | 9/1999 | Holm et al. |
| 5,958,187 A | 9/1999 | Bhat et al. |
| 5,962,112 A | 10/1999 | Haynes et al. |
| 5,972,805 A | 10/1999 | Pomplun et al. |
| 5,980,922 A | 11/1999 | Mackey et al. |
| 5,986,004 A | 11/1999 | Pomplun et al. |
| 5,990,377 A | 11/1999 | Chen et al. |
| 5,993,433 A | 11/1999 | St. Louis et al. |

(56) References Cited

U.S. PATENT DOCUMENTS

| | | |
|---|---|---|
| 6,001,381 A | 12/1999 | Gordon et al. |
| 6,001,751 A | 12/1999 | Pereira et al. |
| 6,007,653 A | 12/1999 | Pirinen et al. |
| 6,013,349 A | 1/2000 | Takeuchi et al. |
| 6,107,833 A | 1/2000 | Reiner et al. |
| 6,022,550 A | 2/2000 | Watanabe |
| 6,037,282 A | 3/2000 | Milding et al. |
| 6,039,839 A | 3/2000 | Trokhan et al. |
| 6,043,317 A | 3/2000 | Mumick et al. |
| 6,050,985 A | 4/2000 | Lavon et al. |
| 6,054,202 A | 4/2000 | Takeuchi et al. |
| 6,059,764 A | 5/2000 | Osborn, III et al. |
| 6,059,928 A | 5/2000 | Van Luu et al. |
| 6,087,551 A | 7/2000 | Pereira |
| 6,098,836 A | 8/2000 | Gottselig |
| 6,103,953 A | 8/2000 | Cree et al. |
| 6,107,539 A | 8/2000 | Palumbo et al. |
| 6,129,718 A | 10/2000 | Wada |
| 6,153,209 A | 11/2000 | Vega et al. |
| 6,159,335 A | 12/2000 | Owens et al. |
| 6,159,487 A | 12/2000 | Znaiden et al. |
| 6,159,882 A | 12/2000 | Kean et al. |
| 6,163,943 A | 12/2000 | Johansson et al. |
| 6,165,625 A | 12/2000 | Sommers et al. |
| 6,168,849 B1 | 1/2001 | Braverman et al. |
| 6,171,442 B1 | 1/2001 | Farrington, Jr. et al. |
| 6,171,682 B1 | 1/2001 | Raidel et al. |
| 6,173,140 B1 | 1/2001 | Suzuki et al. |
| 6,176,142 B1 | 1/2001 | Ericson |
| 6,185,502 B1 | 2/2001 | Sumner |
| 6,194,517 B1 | 2/2001 | Pomplun et al. |
| 6,194,631 B1 | 2/2001 | Mitchell et al. |
| 6,217,562 B1 | 4/2001 | Brown et al. |
| 6,217,889 B1 | 4/2001 | Lorenzi et al. |
| 6,222,091 B1 | 4/2001 | Beihoffer et al. |
| 6,231,556 B1 | 5/2001 | Osborn, III |
| 6,248,097 B1 | 6/2001 | Beitz et al. |
| 6,258,196 B1 | 7/2001 | Suzuki et al. |
| 6,258,308 B1 | 7/2001 | Brady et al. |
| 6,258,996 B1 | 7/2001 | Goldman |
| 6,261,679 B1 | 7/2001 | Chen et al. |
| 6,267,975 B1 | 7/2001 | Smith, III et al. |
| 6,287,288 B1 | 9/2001 | Osborn, III et al. |
| 6,291,372 B1 | 9/2001 | Mumick et al. |
| 6,305,920 B1 | 10/2001 | Kean et al. |
| 6,315,864 B2 | 11/2001 | Anderson et al. |
| 6,344,109 B1 | 2/2002 | Gross |
| 6,346,506 B1 | 2/2002 | Julemont |
| 6,348,253 B1 | 2/2002 | Daley et al. |
| 6,361,784 B1 | 3/2002 | Brennan et al. |
| 6,371,950 B1 | 4/2002 | Roslansky et al. |
| 6,376,443 B1 | 4/2002 | Julemont |
| 6,380,152 B1 | 4/2002 | Julemont et al. |
| 6,380,456 B1 | 4/2002 | Goldman |
| 6,381,817 B1 | 5/2002 | Moody, III |
| 6,392,116 B1 | 5/2002 | Beihoffer et al. |
| 6,395,957 B1 | 5/2002 | Chen et al. |
| 6,407,018 B1 | 6/2002 | Zafirogiu |
| 6,410,499 B1 | 6/2002 | Julemont et al. |
| 6,420,625 B1 | 7/2002 | Jones et al. |
| 6,423,179 B1 | 7/2002 | Jardeby et al. |
| 6,423,804 B1 | 7/2002 | Chang et al. |
| 6,428,799 B1 | 8/2002 | Cen et al. |
| 6,429,182 B1 | 8/2002 | Julemont et al. |
| 6,429,183 B1 | 8/2002 | Leonard et al. |
| 6,429,261 B1 | 8/2002 | Lang et al. |
| 6,433,243 B1 | 8/2002 | Woltman et al. |
| 6,433,244 B1 | 8/2002 | Roe et al. |
| 6,436,234 B1 | 8/2002 | Chen et al. |
| 6,436,892 B1 | 8/2002 | Leonard et al. |
| 6,444,214 B1 | 9/2002 | Cole et al. |
| 6,447,643 B2 | 9/2002 | Fingal et al. |
| 6,452,064 B1 | 9/2002 | Thoren et al. |
| 6,464,831 B1 | 10/2002 | Trokhan et al. |
| 6,465,047 B1 | 10/2002 | Scott et al. |
| 6,475,315 B1 | 11/2002 | Kean et al. |
| 6,475,976 B1 | 11/2002 | Mahieu et al. |
| 6,479,105 B2 | 11/2002 | Chang et al. |
| 6,479,150 B1 | 11/2002 | Liu et al. |
| 6,485,667 B1 | 11/2002 | Tan |
| 6,486,379 B1 | 11/2002 | Chen et al. |
| 6,491,928 B1 | 12/2002 | Smith, III |
| 6,491,933 B2 | 12/2002 | Lorenzi et al. |
| 6,492,574 B1 | 12/2002 | Chen et al. |
| 6,495,508 B1 | 12/2002 | Leonard et al. |
| 6,503,233 B1 | 1/2003 | Chen et al. |
| 6,506,873 B1 | 1/2003 | Ryan et al. |
| 6,509,284 B1 | 1/2003 | Quincy, III et al. |
| 6,516,502 B1 | 2/2003 | Moody, III |
| 6,520,947 B1 | 2/2003 | Tilly et al. |
| 6,524,442 B2 | 2/2003 | Tanner et al. |
| 6,530,910 B1 | 3/2003 | Pomplun et al. |
| 6,533,898 B2 | 3/2003 | Gross |
| 6,533,978 B1 | 3/2003 | Wisneski et al. |
| 6,533,989 B1 | 3/2003 | Wisneski et al. |
| 6,537,631 B1 | 3/2003 | Rivera et al. |
| 6,537,663 B1 | 3/2003 | Chang et al. |
| 6,548,147 B1 | 4/2003 | Raidel et al. |
| 6,548,592 B1 | 4/2003 | Lang et al. |
| 6,550,633 B2 | 4/2003 | Huang et al. |
| 6,555,502 B1 | 4/2003 | Beihoffer et al. |
| 6,562,192 B1 | 5/2003 | Hamilton et al. |
| 6,570,054 B1 | 5/2003 | Gatto et al. |
| 6,572,735 B1 | 6/2003 | Wallajapet et al. |
| 6,576,575 B2 | 6/2003 | Griesbach, III et al. |
| 6,579,570 B1 | 6/2003 | Lang et al. |
| 6,586,529 B2 | 7/2003 | Mumick et al. |
| 6,592,713 B2 | 7/2003 | Ahoniemi |
| 6,596,681 B1 | 7/2003 | Mahieu et al. |
| 6,596,921 B2 | 7/2003 | Beihoffer et al. |
| 6,599,848 B1 | 7/2003 | Chen et al. |
| 6,602,955 B2 | 8/2003 | Soerens et al. |
| 6,603,054 B2 | 8/2003 | Chen et al. |
| 6,608,237 B1 | 8/2003 | Li et al. |
| 6,610,173 B1 | 8/2003 | Lindsay et al. |
| 6,612,462 B2 | 9/2003 | Sosalla et al. |
| 6,613,954 B1 | 9/2003 | Horney et al. |
| 6,623,576 B2 | 9/2003 | Mitchell et al. |
| 6,629,965 B2 | 10/2003 | Drevik et al. |
| 6,630,558 B2 | 10/2003 | Chang et al. |
| 6,638,611 B2 | 10/2003 | Seth |
| 6,643,994 B1 | 11/2003 | Divo et al. |
| 6,647,549 B2 | 11/2003 | McDevitt et al. |
| 6,653,406 B1 | 11/2003 | Soerens et al. |
| 6,659,391 B1 | 12/2003 | Faulks et al. |
| 6,660,362 B1 | 12/2003 | Lindsay et al. |
| 6,660,903 B1 | 12/2003 | Chen et al. |
| 6,667,424 B1 | 12/2003 | Hamilton et al. |
| 6,670,521 B2 | 12/2003 | Noda et al. |
| 6,673,418 B1 | 1/2004 | DeOlivera et al. |
| 6,673,982 B1 | 1/2004 | Chen et al. |
| 6,677,498 B2 | 1/2004 | Chen et al. |
| 6,680,264 B2 | 1/2004 | Julemont |
| 6,682,013 B1 | 1/2004 | Newman et al. |
| 6,683,143 B1 | 1/2004 | Mumick et al. |
| 6,689,931 B2 | 2/2004 | Etheredge, III |
| 6,689,935 B2 | 2/2004 | Chen et al. |
| 6,695,827 B2 | 2/2004 | Chen et al. |
| 6,700,034 B1 | 3/2004 | Lindsay et al. |
| 6,701,637 B2 | 3/2004 | Lindsay et al. |
| 6,702,227 B1 | 3/2004 | Newman et al. |
| 6,706,352 B2 | 3/2004 | Rivera et al. |
| 6,710,222 B2 | 3/2004 | Shimada et al. |
| 6,710,223 B1 | 3/2004 | Van Rijswijck et al. |
| 6,713,411 B2 | 3/2004 | Cox et al. |
| 6,713,414 B1 | 3/2004 | Pomplun et al. |
| 6,721,987 B2 | 4/2004 | McDevitt et al. |
| 6,745,975 B2 | 6/2004 | Faulks et al. |
| 6,749,083 B2 | 6/2004 | Sosalla et al. |
| 6,761,712 B2 | 7/2004 | Otsubo et al. |
| 6,762,138 B2 | 7/2004 | Ferreira et al. |
| 6,770,204 B1 | 8/2004 | Koslow |
| 6,773,545 B2 | 8/2004 | Tanner et al. |
| 6,773,797 B1 | 8/2004 | Wang et al. |

(56) References Cited

U.S. PATENT DOCUMENTS

| | | | |
|---|---|---|---|
| 6,776,947 B2 | 8/2004 | Brady et al. |
| 6,782,589 B2 | 8/2004 | Ngai |
| 6,785,946 B2 | 9/2004 | Romme et al. |
| 6,790,798 B1 | 9/2004 | Suzuki et al. |
| 6,793,930 B2 | 9/2004 | Gatto et al. |
| 6,794,318 B2 | 9/2004 | Anderson et al. |
| 6,802,834 B2 | 10/2004 | Melius et al. |
| 6,803,496 B2 | 10/2004 | Elder et al. |
| 6,808,790 B2 | 10/2004 | Chen et al. |
| 6,811,338 B1 | 11/2004 | Manske et al. |
| 6,814,974 B2 | 11/2004 | Cole et al. |
| 6,820,837 B2 | 11/2004 | Long |
| 6,821,601 B2 | 11/2004 | Tsiarkezos et al. |
| 6,824,650 B2 | 11/2004 | Lindsay et al. |
| 6,827,302 B2 | 12/2004 | Hohnen et al. |
| 6,827,309 B1 | 12/2004 | Newman et al. |
| 6,827,818 B2 | 12/2004 | Farrington, Jr. et al. |
| 6,828,014 B2 | 12/2004 | Branham et al. |
| 6,835,678 B2 | 12/2004 | Jackson et al. |
| 6,837,956 B2 | 1/2005 | Cowell et al. |
| 6,838,040 B2 | 1/2005 | Mlinar et al. |
| 6,843,949 B2 | 1/2005 | Brady et al. |
| 6,844,066 B2 | 1/2005 | Hamed |
| 6,844,303 B2 | 1/2005 | Lange |
| 6,844,308 B1 | 1/2005 | Dastbaz et al. |
| 6,848,595 B2 | 2/2005 | Lange et al. |
| 6,849,157 B2 | 2/2005 | Farrington, Jr. et al. |
| 6,855,790 B2 | 2/2005 | Chang et al. |
| 6,865,784 B2 | 3/2005 | Noelle |
| 6,883,193 B2 | 4/2005 | Brooks et al. |
| 6,888,046 B2 | 5/2005 | Toyoshima et al. |
| 6,897,168 B2 | 5/2005 | Branham et al. |
| 6,905,748 B2 | 6/2005 | Sosalla |
| 6,908,664 B2 | 6/2005 | Tsiarkezos |
| 6,908,966 B2 | 6/2005 | Chang et al. |
| 6,911,114 B2 | 6/2005 | Lindsay et al. |
| 6,911,573 B2 | 6/2005 | Chen et al. |
| 6,916,480 B2 | 7/2005 | Anderson et al. |
| 6,942,726 B2 | 9/2005 | Cook et al. |
| 6,960,371 B2 | 11/2005 | Bunyard et al. |
| 6,986,897 B1 | 1/2006 | Roberts et al. |
| 6,987,075 B2 | 1/2006 | Orlandi |
| 6,989,125 B2 | 1/2006 | Boney et al. |
| 6,989,339 B2 | 1/2006 | Eden et al. |
| 6,991,840 B2 | 1/2006 | Sosalla |
| 6,993,805 B2 | 2/2006 | Prodoehl et al. |
| 6,994,696 B2 | 2/2006 | Suga |
| 6,994,865 B2 | 2/2006 | Branham et al. |
| 6,998,017 B2 | 2/2006 | Lindsay et al. |
| 6,998,086 B2 | 2/2006 | Lake et al. |
| 7,000,363 B2 | 2/2006 | Sosalla et al. |
| 7,005,558 B1 | 2/2006 | Johansson et al. |
| 7,008,620 B2 | 3/2006 | Sun et al. |
| 7,011,272 B2 | 3/2006 | Faulks et al. |
| 7,012,169 B2 | 3/2006 | McDevitt et al. |
| 7,033,645 B2 | 4/2006 | Gatto et al. |
| 7,063,245 B2 | 6/2006 | Faulks et al. |
| 7,070,143 B2 | 7/2006 | Faulks et al. |
| 7,070,854 B2 | 7/2006 | Chang et al. |
| 7,078,087 B2 | 7/2006 | Romano, III et al. |
| 7,081,080 B2 | 7/2006 | Sosalla et al. |
| 7,094,743 B2 | 8/2006 | Thioliere et al. |
| 7,101,456 B2 | 9/2006 | Bunyard et al. |
| 7,101,612 B2 | 9/2006 | Lang et al. |
| 7,102,054 B1 | 9/2006 | Cree et al. |
| 7,115,535 B1 | 10/2006 | Smith, III et al. |
| 7,127,771 B2 | 10/2006 | McDevitt et al. |
| 7,132,377 B2 | 11/2006 | Borgonjon et al. |
| 7,141,108 B2 | 11/2006 | Eden et al. |
| 7,141,519 B2 | 11/2006 | Bunyard et al. |
| 7,156,954 B2 | 1/2007 | Farrington, Jr. et al. |
| 7,157,389 B2 | 1/2007 | Branham et al. |
| 7,163,692 B2 | 1/2007 | Lagatol et al. |
| 7,179,772 B2 | 2/2007 | Keenan et al. |
| 7,186,318 B2 | 3/2007 | Liu et al. |
| 7,186,451 B2 | 3/2007 | Zafiroglu et al. |
| 7,189,448 B2 | 3/2007 | Raidel et al. |
| 7,194,788 B2 | 3/2007 | Clark et al. |
| 7,194,789 B2 | 3/2007 | Thomaschefsky et al. |
| 7,214,633 B2 | 5/2007 | Sun et al. |
| 7,225,476 B2 | 6/2007 | Cerbini et al. |
| 7,225,496 B2 | 6/2007 | Prodoehl et al. |
| 7,228,586 B2 | 6/2007 | Prodoehl et al. |
| 7,235,250 B2 | 6/2007 | Padlo et al. |
| 7,241,711 B2 * | 7/2007 | Takai ............... D21H 25/005 |
| | | 162/147 |
| 7,247,360 B1 | 7/2007 | Besner et al. |
| 7,264,861 B2 | 9/2007 | Zafiroglu et al. |
| 7,265,258 B2 | 9/2007 | Hamilton et al. |
| 7,275,276 B2 | 10/2007 | Jaszenovics et al. |
| 7,276,459 B1 | 10/2007 | Lang et al. |
| 7,278,137 B1 | 10/2007 | Petersen |
| 7,278,988 B2 | 10/2007 | Molas et al. |
| 7,285,504 B2 | 10/2007 | Jones et al. |
| 7,294,376 B2 | 11/2007 | Rivera et al. |
| 7,300,547 B2 | 11/2007 | Luu et al. |
| 7,303,092 B2 | 12/2007 | Sarbo et al. |
| 7,306,813 B2 | 12/2007 | Eden et al. |
| 7,309,132 B2 | 12/2007 | McKay |
| 7,318,498 B2 | 1/2008 | Woodman et al. |
| 7,320,831 B2 | 1/2008 | Farwaha et al. |
| 7,323,072 B2 | 1/2008 | Engelhart et al. |
| 7,323,438 B2 | 1/2008 | Hedges et al. |
| 7,326,318 B2 | 2/2008 | Strandqvist |
| 7,329,705 B2 | 2/2008 | Farwaha et al. |
| 7,331,091 B2 | 2/2008 | Strandqvist |
| 7,333,020 B2 | 2/2008 | Cohen et al. |
| 7,344,526 B2 | 3/2008 | Yang et al. |
| 7,347,914 B2 | 3/2008 | Umebayashi et al. |
| 7,350,256 B2 | 4/2008 | Benjamin et al. |
| 7,357,833 B2 | 4/2008 | Cook et al. |
| 7,358,204 B2 | 4/2008 | Brennan |
| 7,364,380 B2 | 4/2008 | McKay |
| 7,377,001 B2 | 5/2008 | McKay |
| 7,378,360 B2 | 5/2008 | Clark et al. |
| 7,396,584 B2 | 7/2008 | Azad et al. |
| 7,396,782 B2 | 7/2008 | Blenke et al. |
| 7,409,753 B2 | 8/2008 | Li |
| 7,422,660 B2 | 9/2008 | Billgren et al. |
| 7,429,689 B2 | 9/2008 | Chen et al. |
| 7,431,715 B2 | 10/2008 | Guidotti et al. |
| 7,432,219 B2 | 10/2008 | Strandqvist et al. |
| 7,435,266 B2 | 10/2008 | Sun et al. |
| 7,445,615 B2 | 11/2008 | Mizutani et al. |
| 7,446,082 B2 | 11/2008 | Kilkenny et al. |
| 7,452,547 B2 | 11/2008 | Lambino et al. |
| 7,452,835 B2 | 11/2008 | Bridges |
| 7,456,117 B2 | 11/2008 | Branham et al. |
| 7,458,540 B2 | 12/2008 | Weber et al. |
| 7,462,348 B2 | 12/2008 | Gruenbacher et al. |
| 7,462,385 B2 | 12/2008 | Seth et al. |
| 7,465,266 B2 | 12/2008 | Lange et al. |
| 7,465,684 B2 | 12/2008 | Hurley et al. |
| 7,470,652 B2 | 12/2008 | Kilkenny et al. |
| 7,476,221 B2 | 1/2009 | Sun et al. |
| 7,476,222 B2 | 1/2009 | Sun et al. |
| 7,476,631 B2 | 1/2009 | Barnholtz et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,484,276 B2 | 2/2009 | Jeambar |
| 7,485,589 B2 | 2/2009 | Ellis |
| 7,488,310 B2 | 2/2009 | Yang |
| 7,490,382 B2 | 2/2009 | Benjamin et al. |
| 7,491,196 B2 | 2/2009 | Franke et al. |
| 7,504,550 B2 | 3/2009 | Tippey et al. |
| 7,507,047 B2 | 3/2009 | Oberstadt et al. |
| 7,514,591 B2 | 4/2009 | Przepasniak et al. |
| 7,517,166 B2 | 4/2009 | Keck |
| 7,517,556 B2 | 4/2009 | Johnson et al. |
| 7,543,423 B2 | 6/2009 | Long et al. |
| 7,549,178 B2 | 6/2009 | Lin et al. |
| 7,549,188 B2 | 6/2009 | McDevitt et al. |

(56) References Cited

U.S. PATENT DOCUMENTS

| | | |
|---|---|---|
| 7,552,501 B2 | 6/2009 | Yang et al. |
| 7,562,427 B2 | 7/2009 | Nguyen |
| 7,563,733 B2 | 7/2009 | Ahluwalia et al. |
| 7,571,832 B2 | 8/2009 | Mark et al. |
| 7,572,525 B2 | 8/2009 | McDonald |
| 7,578,810 B2 | 8/2009 | Rosenfeld et al. |
| 7,579,078 B2 | 8/2009 | Hartmann et al. |
| 7,582,074 B2 | 9/2009 | Rosenfeld et al. |
| 7,582,240 B2 | 9/2009 | Marin et al. |
| 7,585,797 B2 | 9/2009 | Vogel et al. |
| 7,587,798 B2 | 9/2009 | Michalon et al. |
| 7,592,049 B2 | 9/2009 | Jones et al. |
| 7,592,391 B2 | 9/2009 | Calhoun et al. |
| 7,594,904 B2 | 9/2009 | Rosenfeld et al. |
| 7,604,623 B2 | 10/2009 | Brunner et al. |
| 7,604,859 B2 | 10/2009 | Liu et al. |
| 7,608,070 B2 | 10/2009 | Chen et al. |
| 7,611,501 B2 | 11/2009 | Luizzi |
| 7,615,039 B2 | 11/2009 | Rosenfeld et al. |
| 7,619,033 B2 | 11/2009 | Calhoun et al. |
| 7,629,043 B2 | 12/2009 | Lindsay et al. |
| 7,640,637 B2 | 1/2010 | Efremova et al. |
| 7,642,395 B2 | 1/2010 | Schroeder et al. |
| 7,645,353 B2 | 1/2010 | Thomaschefsky et al. |
| 7,647,667 B2 | 1/2010 | Bejamin et al. |
| 7,651,290 B2 | 1/2010 | Bauer et al. |
| 7,654,992 B2 | 2/2010 | Yamaki et al. |
| 7,655,212 B2 | 2/2010 | Sandford et al. |
| 7,662,460 B2 | 2/2010 | Herfert et al. |
| 7,662,462 B2 | 2/2010 | Noda et al. |
| 7,665,176 B2 | 2/2010 | Benjamin et al. |
| 7,666,448 B2 | 2/2010 | Mower |
| 7,670,459 B2 | 3/2010 | Garnier et al. |
| 7,670,967 B2 | 3/2010 | Runge et al. |
| 7,670,971 B2 | 3/2010 | Brennan |
| 7,674,058 B2 | 3/2010 | Berger Sharp et al. |
| 7,678,231 B2 | 3/2010 | Dyer et al. |
| 7,684,939 B2 | 3/2010 | Allende-Blanco et al. |
| 7,686,796 B2 | 3/2010 | Kuen et al. |
| 7,687,681 B2 | 3/2010 | Di Luccio |
| 7,695,461 B2 | 4/2010 | Rosenfeld et al. |
| 7,696,109 B2 | 4/2010 | Ouellette et al. |
| 7,704,241 B2 | 4/2010 | Rosenfeld et al. |
| 7,718,249 B2 | 5/2010 | Russell et al. |
| 7,722,589 B2 | 5/2010 | Fitts, Jr. et al. |
| 7,727,212 B2 | 6/2010 | Sakai et al. |
| 7,732,036 B2 | 6/2010 | Etchells |
| 7,732,357 B2 | 6/2010 | Annis et al. |
| 7,745,356 B2 | 6/2010 | Blenke et al. |
| 7,745,687 B2 | 6/2010 | Heyn et al. |
| 7,753,896 B2 | 7/2010 | Collado et al. |
| 7,758,724 B2 | 7/2010 | Akai et al. |
| 7,758,945 B2 | 7/2010 | Noelle |
| 7,758,947 B2 | 7/2010 | Maschino et al. |
| 7,767,058 B2 | 8/2010 | Walton et al. |
| 7,767,878 B2 | 8/2010 | Suzuki |
| 7,772,138 B2 | 8/2010 | Lostocco et al. |
| 7,776,772 B2 | 8/2010 | Barnholtz et al. |
| 7,785,306 B2 | 8/2010 | Poccia et al. |
| 7,785,764 B2 | 8/2010 | Williams |
| 7,790,282 B2 | 9/2010 | Hartmann et al. |
| 7,799,967 B2 | 9/2010 | Ranganathan et al. |
| 7,799,968 B2 | 9/2010 | Chen et al. |
| 7,803,244 B2 | 9/2010 | Siqueira et al. |
| 7,803,249 B2 | 9/2010 | Dyer et al. |
| 7,803,250 B2 | 9/2010 | Dyer et al. |
| 7,807,023 B2 | 10/2010 | Dyer et al. |
| 7,807,118 B2 | 10/2010 | Green et al. |
| 7,811,270 B2 | 10/2010 | Rosenfeld et al. |
| 7,814,625 B2 | 10/2010 | Russell et al. |
| 7,816,287 B1 | 10/2010 | Hartgrove |
| 7,819,911 B2 | 10/2010 | Anderson et al. |
| 7,820,149 B2 | 10/2010 | Cunningham et al. |
| 7,829,478 B2 | 11/2010 | Johnson et al. |
| 7,829,611 B2 | 11/2010 | Kelly |
| 7,837,832 B2 | 11/2010 | Fetner et al. |
| 7,838,111 B2 | 11/2010 | Fish et al. |
| 7,838,725 B2 | 11/2010 | Noda et al. |
| 7,846,296 B2 | 12/2010 | Luu et al. |
| 7,851,668 B2 | 12/2010 | Elder et al. |
| 7,855,315 B2 | 12/2010 | Mitchell et al. |
| 7,857,841 B2 | 12/2010 | Anderson et al. |
| 7,861,964 B2 | 1/2011 | Cittadino et al. |
| 7,862,599 B2 | 1/2011 | Anderson |
| 7,871,429 B2 | 1/2011 | Anderson et al. |
| 7,875,014 B2 | 1/2011 | Hendren et al. |
| 7,879,188 B2 | 2/2011 | Dyer et al. |
| 7,879,189 B2 | 2/2011 | Dyer et al. |
| 7,879,190 B2 | 2/2011 | Dyer et al. |
| 7,879,191 B2 | 2/2011 | Dyer et al. |
| 7,879,745 B2 | 2/2011 | Blenke et al. |
| 7,884,037 B2 | 2/2011 | Sirovatka et al. |
| 7,914,566 B2 | 3/2011 | Anderson et al. |
| 7,917,985 B2 | 4/2011 | Dorsey et al. |
| 7,919,419 B2 | 4/2011 | Hurley et al. |
| 7,922,861 B2 | 4/2011 | Blenke et al. |
| 7,927,322 B2 | 4/2011 | Cohen et al. |
| 7,928,282 B2 | 4/2011 | Dibb et al. |
| 7,931,638 B2 | 4/2011 | Yao et al. |
| 7,931,880 B2 | 4/2011 | Sandford et al. |
| 7,943,165 B2 | 5/2011 | Doney et al. |
| 7,947,027 B2 | 5/2011 | VanDenBogart et al. |
| 7,947,314 B2 | 5/2011 | Nam |
| 7,947,613 B2 | 5/2011 | Ouellette et al. |
| 7,950,864 B2 | 5/2011 | Bauer et al. |
| 7,951,127 B2 | 5/2011 | Sanabria et al. |
| 7,976,525 B2 | 7/2011 | McDaniel |
| 7,976,662 B2 | 7/2011 | Thomas et al. |
| 7,984,829 B2 | 7/2011 | Cittadino et al. |
| 7,985,209 B2 | 7/2011 | Villanueva et al. |
| 7,988,779 B2 | 8/2011 | Disalvo et al. |
| 7,988,860 B2 | 8/2011 | Kalayci et al. |
| 7,989,545 B2 | 8/2011 | Farwaha et al. |
| 7,993,322 B2 | 8/2011 | Brud et al. |
| 7,994,079 B2 | 8/2011 | Chen et al. |
| 7,994,386 B2 | 8/2011 | Tokura et al. |
| 7,996,108 B2 | 8/2011 | Yardley |
| 7,998,388 B2 | 8/2011 | Marin et al. |
| 7,999,031 B2 | 8/2011 | Calhoun et al. |
| 8,012,137 B2 | 9/2011 | Lira et al. |
| 8,021,996 B2 | 9/2011 | Walser et al. |
| 8,029,489 B2 | 10/2011 | Yu et al. |
| 8,033,421 B2 | 10/2011 | Cowell et al. |
| 8,044,256 B2 | 10/2011 | Gatto et al. |
| 8,044,258 B2 | 10/2011 | Hietpas |
| 8,058,500 B2 | 11/2011 | Sojka et al. |
| 8,062,275 B2 | 11/2011 | Plentovich et al. |
| 8,062,615 B2 | 11/2011 | Sandford et al. |
| 8,066,217 B2 | 11/2011 | Cittadino et al. |
| 8,066,444 B2 | 11/2011 | Rippl et al. |
| 8,066,956 B2 | 11/2011 | Do et al. |
| 8,075,722 B2 | 12/2011 | Takahashi et al. |
| 8,079,992 B2 | 12/2011 | Bissah et al. |
| 8,080,076 B2 | 12/2011 | Sauer et al. |
| 8,080,216 B2 | 12/2011 | Green et al. |
| 8,080,489 B2 | 12/2011 | Brennan |
| 8,092,442 B2 | 1/2012 | Sukegawa |
| 8,092,691 B2 | 1/2012 | Youngs et al. |
| 8,092,814 B2 | 1/2012 | Borysewicz et al. |
| 8,100,130 B2 | 1/2012 | Allen et al. |
| 8,105,463 B2 | 1/2012 | Goulet et al. |
| 8,123,905 B2 | 2/2012 | Luu et al. |
| 8,124,061 B2 | 2/2012 | Lam et al. |
| 8,129,450 B2 | 3/2012 | Wood et al. |
| 8,132,575 B2 | 3/2012 | Tojo et al. |
| 8,133,825 B2 | 3/2012 | Bunyard et al. |
| 8,133,991 B2 | 3/2012 | Nonomura et al. |
| 8,137,790 B2 | 3/2012 | Dharmadhikary et al. |
| 8,138,388 B2 | 3/2012 | Eider et al. |
| 8,150,525 B2 | 4/2012 | Fassih et al. |
| 8,153,574 B2 | 4/2012 | Boutique et al. |
| 8,156,576 B1 | 4/2012 | Terrell |
| 8,157,780 B2 | 4/2012 | Lira et al. |
| 8,158,689 B2 | 4/2012 | Baker et al. |

(56) References Cited

U.S. PATENT DOCUMENTS

| | | |
|---|---|---|
| 8,165,716 B1 | 4/2012 | Goeking et al. |
| 8,173,153 B2 | 5/2012 | Rosato et al. |
| 8,173,257 B2 | 5/2012 | Hartmann et al. |
| 8,178,600 B2 | 5/2012 | Kelly |
| 8,183,431 B2 | 5/2012 | Noda et al. |
| 8,187,242 B1 | 5/2012 | Raidel et al. |
| 8,192,475 B2 | 6/2012 | Anderson et al. |
| 8,197,455 B2 | 6/2012 | Zander et al. |
| 8,197,456 B2 | 6/2012 | Van Himbergen et al. |
| 8,202,609 B2 | 6/2012 | Ducker et al. |
| 8,211,075 B2 | 7/2012 | Noda et al. |
| 8,222,023 B2 | 7/2012 | Battrell et al. |
| 8,225,469 B2 | 7/2012 | Bevan |
| 8,227,658 B2 | 7/2012 | Shi et al. |
| 8,230,969 B2 | 7/2012 | Frederick et al. |
| 8,231,590 B2 | 7/2012 | Zander et al. |
| 8,232,334 B2 | 7/2012 | Kelly et al. |
| 8,232,345 B2 | 7/2012 | Farwaha et al. |
| 8,235,960 B2 | 8/2012 | Tatsukawa et al. |
| 8,241,743 B2 | 8/2012 | Brennan |
| 8,250,719 B2 | 8/2012 | Ouellette |
| 8,251,969 B2 | 8/2012 | Van Den Bogart et al. |
| 8,257,331 B2 | 9/2012 | Fujioka et al. |
| 8,257,553 B2 | 9/2012 | Zwick et al. |
| 8,263,214 B2 | 9/2012 | Kalayci et al. |
| 9,005,395 B1 | 4/2015 | Zwick et al. |
| 2001/0008180 A1 | 7/2001 | Anderson et al. |
| 2001/0013389 A1 | 8/2001 | Fingal et al. |
| 2001/0018068 A1 | 8/2001 | Lorenzi et al. |
| 2001/0021458 A1 | 9/2001 | Campbell et al. |
| 2001/0024716 A1 | 9/2001 | Chen et al. |
| 2001/0031358 A1 | 10/2001 | Tan et al. |
| 2001/0031595 A1 | 10/2001 | Anderson et al. |
| 2001/0036787 A1 | 11/2001 | Brennan |
| 2001/0039786 A1 | 11/2001 | Romme et al. |
| 2001/0041487 A1 | 11/2001 | Brady et al. |
| 2001/0051796 A1 | 12/2001 | Noda et al. |
| 2001/0056269 A1 | 12/2001 | Shimada et al. |
| 2002/0005452 A1 | 1/2002 | Romme et al. |
| 2002/0006886 A1 | 1/2002 | Beerse et al. |
| 2002/0007166 A1 | 1/2002 | Mitchell et al. |
| 2002/0022050 A1 | 2/2002 | Anderson et al. |
| 2002/0023932 A1 | 2/2002 | Faulks et al. |
| 2002/0026165 A1 | 2/2002 | Elder et al. |
| 2002/0036208 A1 | 3/2002 | Faulks et al. |
| 2002/0040210 A1 | 4/2002 | Luccio et al. |
| 2002/0040213 A1 | 4/2002 | Tweddell, III et al. |
| 2002/0056785 A1 | 5/2002 | Newman et al. |
| 2002/0059993 A1 | 5/2002 | Tanner et al. |
| 2002/0066209 A1 | 6/2002 | Steed et al. |
| 2002/0068160 A1 | 6/2002 | Joyce |
| 2002/0074097 A1 | 6/2002 | Gross |
| 2002/0077613 A1 | 6/2002 | Molas |
| 2002/0077614 A1 | 6/2002 | Molas |
| 2002/0077618 A1 | 6/2002 | Molas |
| 2002/0078538 A1 | 6/2002 | Ngai |
| 2002/0081930 A1 | 6/2002 | Jackson et al. |
| 2002/0082578 A1 | 6/2002 | Otsubo et al. |
| 2002/0087134 A1 | 7/2002 | Drevik et al. |
| 2002/0088099 A1 | 7/2002 | Ahoniemi |
| 2002/0088815 A1 | 7/2002 | Faulks et al. |
| 2002/0096295 A1 | 7/2002 | Jardeby et al. |
| 2002/0099347 A1 | 7/2002 | Chen et al. |
| 2002/0103469 A1 | 8/2002 | Chen et al. |
| 2002/0107156 A1 | 8/2002 | Shaw et al. |
| 2002/0107495 A1 | 8/2002 | Chen et al. |
| 2002/0111450 A1 | 8/2002 | Chang et al. |
| 2002/0111596 A1 | 8/2002 | Fletcher et al. |
| 2002/0119721 A1 | 8/2002 | Panandiker et al. |
| 2002/0132548 A1 | 9/2002 | Ferreira et al. |
| 2002/0133131 A1 | 9/2002 | Rangachari et al. |
| 2002/0143304 A1 | 10/2002 | Elder et al. |
| 2002/0146552 A1 | 10/2002 | Mumick et al. |
| 2002/0147433 A1 | 10/2002 | McOsker et al. |
| 2002/0152538 A1 | 10/2002 | McDevitt et al. |
| 2002/0152630 A1 | 10/2002 | Lindsay et al. |
| 2002/0155234 A1 | 10/2002 | Seth |
| 2002/0155281 A1 | 10/2002 | Lang et al. |
| 2002/0165508 A1 | 11/2002 | Klofta et al. |
| 2002/0170133 A1 | 11/2002 | McDevitt et al. |
| 2002/0176877 A1 | 11/2002 | Cole et al. |
| 2002/0177827 A1 | 11/2002 | Noda et al. |
| 2002/0192268 A1 | 12/2002 | Alwattari et al. |
| 2002/0192407 A1 | 12/2002 | Hendrix et al. |
| 2002/0192433 A1 | 12/2002 | Huang et al. |
| 2002/0195764 A1 | 12/2002 | Sosalla et al. |
| 2003/0000665 A1* | 1/2003 | Takai .................. D21H 25/005 162/115 |
| 2003/0010789 A1 | 1/2003 | Sosalla et al. |
| 2003/0013365 A1 | 1/2003 | Julemont |
| 2003/0014027 A1 | 1/2003 | Beihoffer et al. |
| 2003/0019961 A1 | 1/2003 | Hohnen et al. |
| 2003/0021947 A1 | 1/2003 | Tsiarkezos et al. |
| 2003/0022568 A1 | 1/2003 | Branham et al. |
| 2003/0022781 A1 | 1/2003 | Sosalla et al. |
| 2003/0024062 A1 | 2/2003 | McKay |
| 2003/0024092 A1 | 2/2003 | Orlandi |
| 2003/0024211 A1 | 2/2003 | Käckenmeister et al. |
| 2003/0026963 A1 | 2/2003 | Chang et al. |
| 2003/0027470 A1 | 2/2003 | Chang et al. |
| 2003/0028985 A1 | 2/2003 | Prodoehl et al. |
| 2003/0032352 A1 | 2/2003 | Chang et al. |
| 2003/0045191 A1 | 3/2003 | Goldstein et al. |
| 2003/0045645 A1 | 3/2003 | Chang et al. |
| 2003/0045825 A1 | 3/2003 | Etheredge, III |
| 2003/0049987 A1 | 3/2003 | Close et al. |
| 2003/0050589 A1 | 3/2003 | McDevitt et al. |
| 2003/0050617 A1 | 3/2003 | Chen et al. |
| 2003/0055146 A1 | 3/2003 | Chang et al. |
| 2003/0060105 A1 | 3/2003 | Puckhaber et al. |
| 2003/0070780 A1 | 4/2003 | Chen et al. |
| 2003/0071391 A1 | 4/2003 | Brady et al. |
| 2003/0073362 A1 | 4/2003 | Griesbach, III et al. |
| 2003/0073970 A1 | 4/2003 | Suga |
| 2003/0083631 A1 | 5/2003 | Chen et al. |
| 2003/0084788 A1 | 5/2003 | Fraser, Jr. |
| 2003/0084983 A1 | 5/2003 | Rangachari et al. |
| 2003/0088229 A1 | 5/2003 | Baker et al. |
| 2003/0089475 A1 | 5/2003 | Farrington, Jr. et al. |
| 2003/0089478 A1 | 5/2003 | Tanner et al. |
| 2003/0092792 A1 | 5/2003 | Blenke et al. |
| 2003/0092813 A1 | 5/2003 | Blenke et al. |
| 2003/0093046 A1 | 5/2003 | Kim et al. |
| 2003/0096910 A1 | 5/2003 | Soerens et al. |
| 2003/0097105 A1 | 5/2003 | Chen et al. |
| 2003/0105257 A1 | 6/2003 | Chang et al. |
| 2003/0114324 A1 | 6/2003 | Lange |
| 2003/0114822 A1 | 6/2003 | Collando et al. |
| 2003/0116575 A1 | 6/2003 | Ellingson et al. |
| 2003/0118850 A1 | 6/2003 | McCormack et al. |
| 2003/0119705 A1 | 6/2003 | Barnabas et al. |
| 2003/0121380 A1 | 7/2003 | Cowell et al. |
| 2003/0121530 A1 | 7/2003 | Borgonjon et al. |
| 2003/0129901 A1 | 7/2003 | Cox et al. |
| 2003/0130641 A1 | 7/2003 | Richlen et al. |
| 2003/0131454 A1 | 7/2003 | Noelle |
| 2003/0131962 A1 | 7/2003 | Lindsay et al. |
| 2003/0132549 A1 | 7/2003 | Mlinar et al. |
| 2003/0134075 A1 | 7/2003 | Rivera et al. |
| 2003/0134560 A1 | 7/2003 | Bevan |
| 2003/0135181 A1 | 7/2003 | Chen et al. |
| 2003/0135939 A1 | 7/2003 | Sun et al. |
| 2003/0135947 A1 | 7/2003 | McKay |
| 2003/0139721 A1 | 7/2003 | Melius et al. |
| 2003/0144379 A1 | 7/2003 | Mitchell et al. |
| 2003/0149415 A1 | 8/2003 | Wallajapet et al. |
| 2003/0159213 A1 | 8/2003 | Orlandi |
| 2003/0167044 A1 | 9/2003 | Toyoshima et al. |
| 2003/0168776 A1 | 9/2003 | Brady et al. |
| 2003/0171052 A1 | 9/2003 | Bansal et al. |
| 2003/0171728 A1 | 9/2003 | Heyn et al. |
| 2003/0190336 A1 | 10/2003 | Adams et al. |
| 2003/0192902 A1 | 10/2003 | Sosalla et al. |
| 2003/0194937 A1 | 10/2003 | Bendor et al. |

(56) References Cited

U.S. PATENT DOCUMENTS

| | | |
|---|---|---|
| 2003/0195485 A1 | 10/2003 | Rangachari et al. |
| 2003/0195486 A1 | 10/2003 | Gatto et al. |
| 2003/0203695 A1 | 10/2003 | Polanco et al. |
| 2003/0208175 A1 | 11/2003 | Gross et al. |
| 2003/0213108 A1 | 11/2003 | Strandqvist |
| 2003/0217448 A1 | 11/2003 | Andersen |
| 2003/0220038 A1 | 11/2003 | Tsiarkezos |
| 2003/0220039 A1 | 11/2003 | Chen et al. |
| 2003/0220042 A1 | 11/2003 | Lostocco et al. |
| 2003/0221396 A1 | 12/2003 | Sosalla et al. |
| 2003/0224146 A1 | 12/2003 | Raidel et al. |
| 2003/0228813 A1 | 12/2003 | Johnson et al. |
| 2003/0228822 A1 | 12/2003 | Pereira et al. |
| 2003/0234468 A1 | 12/2003 | Rangachari et al. |
| 2004/0019342 A1 | 1/2004 | Nagasuna et al. |
| 2004/0020614 A1 | 2/2004 | Lindsay et al. |
| 2004/0022833 A1 | 2/2004 | Hartwig et al. |
| 2004/0030080 A1 | 2/2004 | Chang et al. |
| 2004/0033744 A1 | 2/2004 | Eden et al. |
| 2004/0033745 A1 | 2/2004 | Eden et al. |
| 2004/0042965 A1 | 3/2004 | Usui et al. |
| 2004/0043911 A1 | 3/2004 | Shaw et al. |
| 2004/0054331 A1 | 3/2004 | Hamilton et al. |
| 2004/0055704 A1 | 3/2004 | Bunyard et al. |
| 2004/0058073 A1 | 3/2004 | Bunyard et al. |
| 2004/0058600 A1 | 3/2004 | Bunyard et al. |
| 2004/0058606 A1 | 3/2004 | Branham et al. |
| 2004/0060858 A1 | 4/2004 | Lucas et al. |
| 2004/0062732 A1 | 4/2004 | Friscia et al. |
| 2004/0062735 A1 | 4/2004 | Sun et al. |
| 2004/0062791 A1 | 4/2004 | Branham et al. |
| 2004/0062798 A1 | 4/2004 | Lukenbach et al. |
| 2004/0062907 A1 | 4/2004 | Lindsay et al. |
| 2004/0063371 A1 | 4/2004 | Cox et al. |
| 2004/0063603 A1 | 4/2004 | Dave et al. |
| 2004/0063888 A1 | 4/2004 | Bunyard et al. |
| 2004/0064119 A1 | 4/2004 | Guldotti et al. |
| 2004/0065233 A1 | 4/2004 | Cook et al. |
| 2004/0076660 A1 | 4/2004 | Padlo et al. |
| 2004/0086698 A1 | 5/2004 | Collins et al. |
| 2004/0087924 A1 | 5/2004 | Sroda et al. |
| 2004/0087928 A1 | 5/2004 | Ducker |
| 2004/0092185 A1 | 5/2004 | Grafe et al. |
| 2004/0099706 A1 | 5/2004 | Krautkramer et al. |
| 2004/0102122 A1 | 5/2004 | Boney et al. |
| 2004/0102752 A1 | 5/2004 | Chen et al. |
| 2004/0111817 A1 | 6/2004 | Chen et al. |
| 2004/0112508 A1 | 6/2004 | Umebayashi et al. |
| 2004/0115394 A1 | 6/2004 | Lange et al. |
| 2004/0115429 A1 | 6/2004 | Michl et al. |
| 2004/0115431 A1 | 6/2004 | Chen et al. |
| 2004/0116017 A1 | 6/2004 | Smith, III et al. |
| 2004/0118964 A1 | 6/2004 | Long |
| 2004/0121683 A1 | 6/2004 | Jordan et al. |
| 2004/0121686 A1 | 6/2004 | Wong et al. |
| 2004/0126411 A1 | 7/2004 | Lagatol et al. |
| 2004/0127873 A1 | 7/2004 | Varona et al. |
| 2004/0131660 A1 | 7/2004 | Lange et al. |
| 2004/0137200 A1 | 7/2004 | Chhabra et al. |
| 2004/0147189 A1 | 7/2004 | Smith, III et al. |
| 2004/0157032 A1 | 8/2004 | Rivera et al. |
| 2004/0161991 A1 | 8/2004 | Walton et al. |
| 2004/0163674 A1 | 8/2004 | Policicchio et al. |
| 2004/0166281 A1 | 8/2004 | Park |
| 2004/0167479 A1 | 8/2004 | Warren et al. |
| 2004/0170836 A1 | 9/2004 | Bond et al. |
| 2004/0172754 A1 | 9/2004 | Brooks et al. |
| 2004/0177935 A1 | 9/2004 | Hamed et al. |
| 2004/0181201 A1 | 9/2004 | Mizutani et al. |
| 2004/0182531 A1 | 9/2004 | Nomura et al. |
| 2004/0191470 A1 | 9/2004 | Zafiroglu et al. |
| 2004/0192142 A1 | 9/2004 | Zafiroglu et al. |
| 2004/0198114 A1 | 10/2004 | Barnholtz et al. |
| 2004/0198118 A1 | 10/2004 | Levine et al. |
| 2004/0203306 A1 | 10/2004 | Grafe et al. |
| 2004/0204332 A1 | 10/2004 | Dastbaz et al. |
| 2004/0206465 A1 | 10/2004 | Farrington, Jr. et al. |
| 2004/0208984 A1 | 10/2004 | Gatto et al. |
| 2004/0217325 A1 | 11/2004 | Usui et al. |
| 2004/0221437 A1 | 11/2004 | Fleissner |
| 2004/0229054 A1 | 11/2004 | Ahluwalia et al. |
| 2004/0234760 A1 | 11/2004 | Hamed |
| 2004/0234803 A1 | 11/2004 | Joyce |
| 2004/0242097 A1 | 12/2004 | Hasenoehrl et al. |
| 2004/0248492 A1 | 12/2004 | Baker, Jr. |
| 2004/0250969 A1 | 12/2004 | Luu et al. |
| 2004/0253297 A1 | 12/2004 | Hedges et al. |
| 2004/0254086 A1 | 12/2004 | Hedges et al. |
| 2004/0256066 A1 | 12/2004 | Lindsay et al. |
| 2004/0260258 A1 | 12/2004 | Hall et al. |
| 2004/0261208 A1 | 12/2004 | McKay |
| 2004/0261209 A1 | 12/2004 | McKay |
| 2004/0266302 A1 | 12/2004 | DiSalvo et al. |
| 2004/0267223 A1 | 12/2004 | Etchells |
| 2004/0267237 A1 | 12/2004 | Sun et al. |
| 2005/0000669 A1 | 1/2005 | West |
| 2005/0004508 A1 | 1/2005 | Sun et al. |
| 2005/0004509 A1 | 1/2005 | Sun et al. |
| 2005/0004550 A1 | 1/2005 | Sun et al. |
| 2005/0006039 A1 | 1/2005 | Farrington, Jr. et al. |
| 2005/0006399 A1 | 1/2005 | Faulks et al. |
| 2005/0010161 A1 | 1/2005 | Sun et al. |
| 2005/0010192 A1 | 1/2005 | Sun et al. |
| 2005/0013992 A1 | 1/2005 | Azad et al. |
| 2005/0015042 A1 | 1/2005 | Sun et al. |
| 2005/0022309 A1 | 2/2005 | Thioliere et al. |
| 2005/0022954 A1 | 2/2005 | Strandqvist |
| 2005/0027276 A1 | 2/2005 | Collado et al. |
| 2005/0031833 A1 | 2/2005 | Dilnik et al. |
| 2005/0031847 A1 | 2/2005 | Martens et al. |
| 2005/0031850 A1 | 2/2005 | Mitchell et al. |
| 2005/0040179 A1 | 2/2005 | Lange et al. |
| 2005/0042262 A1 | 2/2005 | Hasenoehrl et al. |
| 2005/0042400 A1 | 2/2005 | Cerbini et al. |
| 2005/0042957 A1 | 2/2005 | McDonald et al. |
| 2005/0045290 A1 | 3/2005 | Hamed et al. |
| 2005/0046314 A1 | 3/2005 | Sellars et al. |
| 2005/0048856 A1 | 3/2005 | Hauser et al. |
| 2005/0049565 A1 | 3/2005 | Joseph et al. |
| 2005/0059947 A1 | 3/2005 | Murguly |
| 2005/0059948 A1 | 3/2005 | Murguly |
| 2005/0059949 A1 | 3/2005 | Murguly |
| 2005/0059950 A1 | 3/2005 | Murguly |
| 2005/0061356 A1 | 3/2005 | Wong et al. |
| 2005/0063764 A1 | 3/2005 | McKay |
| 2005/0064058 A1 | 3/2005 | Lake et al. |
| 2005/0066457 A1 | 3/2005 | McKay |
| 2005/0066463 A1 | 3/2005 | Brunner |
| 2005/0066464 A1 | 3/2005 | McKay |
| 2005/0071938 A1 | 4/2005 | McDevitt et al. |
| 2005/0074484 A1 | 4/2005 | Estanislao et al. |
| 2005/0079315 A1 | 4/2005 | Seth et al. |
| 2005/0085150 A1 | 4/2005 | Hamed |
| 2005/0085406 A1 | 4/2005 | Shaw et al. |
| 2005/0091811 A1 | 5/2005 | Billgren et al. |
| 2005/0092417 A1 | 5/2005 | Billgren et al. |
| 2005/0095403 A1 | 5/2005 | Noelle |
| 2005/0095941 A1 | 5/2005 | Coronado et al. |
| 2005/0101207 A1 | 5/2005 | Bonnechere et al. |
| 2005/0112980 A1 | 5/2005 | Strandqvist et al. |
| 2005/0115462 A1 | 6/2005 | Disalvo et al. |
| 2005/0121054 A1 | 6/2005 | Barnabas et al. |
| 2005/0125879 A1 | 6/2005 | Yang et al. |
| 2005/0125923 A1 | 6/2005 | Benjamin et al. |
| 2005/0125924 A1 | 6/2005 | Benjamin et al. |
| 2005/0125926 A1 | 6/2005 | Rekum et al. |
| 2005/0129743 A1 | 6/2005 | Benjamin et al. |
| 2005/0129897 A1 | 6/2005 | Zhou et al. |
| 2005/0129898 A1 | 6/2005 | Sosalla |
| 2005/0130536 A1 | 6/2005 | Siebers et al. |
| 2005/0131371 A1 | 6/2005 | Fell et al. |
| 2005/0131377 A1 | 6/2005 | Franke et al. |
| 2005/0131381 A1 | 6/2005 | Kuen et al. |
| 2005/0131382 A1 | 6/2005 | Brud et al. |

(56) References Cited

U.S. PATENT DOCUMENTS

| | | |
|---|---|---|
| 2005/0132886 A1 | 6/2005 | Schultz et al. |
| 2005/0133177 A1 | 6/2005 | Stralin et al. |
| 2005/0136238 A1 | 6/2005 | Lindsay et al. |
| 2005/0136265 A1 | 6/2005 | Liu et al. |
| 2005/0136772 A1 | 6/2005 | Chen et al. |
| 2005/0136776 A1 | 6/2005 | Clark et al. |
| 2005/0136777 A1 | 6/2005 | Thomaschefsky et al. |
| 2005/0136778 A1 | 6/2005 | Thomaschefsky et al. |
| 2005/0136779 A1 | 6/2005 | Stralin et al. |
| 2005/0136780 A1 | 6/2005 | Clark et al. |
| 2005/0137540 A1 | 6/2005 | Villanueva et al. |
| 2005/0138742 A1 | 6/2005 | Jaszenovics et al. |
| 2005/0139713 A1 | 6/2005 | Weber et al. |
| 2005/0142336 A1 | 6/2005 | Romano, III et al. |
| 2005/0142973 A1 | 6/2005 | Bletsos et al. |
| 2005/0148959 A1 | 7/2005 | Przepasniak et al. |
| 2005/0148980 A1 | 7/2005 | Fitton |
| 2005/0148996 A1 | 7/2005 | Sun et al. |
| 2005/0150784 A1 | 7/2005 | Sanchez et al. |
| 2005/0153123 A1 | 7/2005 | Herfert et al. |
| 2005/0154365 A1 | 7/2005 | Zander et al. |
| 2005/0155628 A1 | 7/2005 | Kilkenny et al. |
| 2005/0155630 A1 | 7/2005 | Kilkenny et al. |
| 2005/0155631 A1 | 7/2005 | Kilkenny et al. |
| 2005/0159063 A1 | 7/2005 | Hill et al. |
| 2005/0160543 A1 | 7/2005 | Catalfamo et al. |
| 2005/0164901 A1 | 7/2005 | Foley et al. |
| 2005/0177122 A1 | 8/2005 | Berba et al. |
| 2005/0178518 A1 | 8/2005 | West et al. |
| 2005/0181200 A1 | 8/2005 | Mertens et al. |
| 2005/0192201 A1 | 9/2005 | Cornelio Ford et al. |
| 2005/0197319 A1 | 9/2005 | Nonomura et al. |
| 2005/0208106 A1 | 9/2005 | Lange et al. |
| 2005/0208853 A1 | 9/2005 | Hendrix et al. |
| 2005/0209396 A1 | 9/2005 | Calhoun et al. |
| 2005/0214507 A1 | 9/2005 | McDonald |
| 2005/0217698 A1 | 10/2005 | Mitchell et al. |
| 2005/0217932 A1 | 10/2005 | Woodman et al. |
| 2005/0222550 A1 | 10/2005 | Mitsui et al. |
| 2005/0226834 A1 | 10/2005 | Lambino et al. |
| 2005/0228350 A1 | 10/2005 | Ranganathan et al. |
| 2005/0229344 A1 | 10/2005 | Mittelstaedt et al. |
| 2005/0239359 A1 | 10/2005 | Jones et al. |
| 2005/0244480 A1 | 11/2005 | Koenig et al. |
| 2005/0244629 A1 | 11/2005 | Usui et al. |
| 2005/0244639 A1 | 11/2005 | Marin et al. |
| 2005/0250402 A1 | 11/2005 | Wild et al. |
| 2005/0256082 A1 | 11/2005 | Nonomura et al. |
| 2005/0256440 A1 | 11/2005 | Zunker et al. |
| 2005/0256471 A1 | 11/2005 | Dibb et al. |
| 2005/0256483 A1 | 11/2005 | Przepasniak et al. |
| 2005/0266229 A1 | 12/2005 | Porticos et al. |
| 2005/0266230 A1 | 12/2005 | Hill et al. |
| 2005/0272335 A1 | 12/2005 | Johnson et al. |
| 2005/0278912 A1 | 12/2005 | Westland et al. |
| 2005/0279473 A1 | 12/2005 | Westland et al. |
| 2005/0282714 A1 | 12/2005 | Oldenhove et al. |
| 2005/0288208 A1 | 12/2005 | Keenan et al. |
| 2005/0288647 A1 | 12/2005 | Ellingson et al. |
| 2006/0003649 A1 | 1/2006 | Runge et al. |
| 2006/0003654 A1 | 1/2006 | Lostocco et al. |
| 2006/0003912 A1 | 1/2006 | Lindsay et al. |
| 2006/0004318 A1 | 1/2006 | Przepasniak et al. |
| 2006/0005336 A1 | 1/2006 | Prodoehl et al. |
| 2006/0010629 A1 | 1/2006 | Prodoehl et al. |
| 2006/0014455 A1 | 1/2006 | Sheffer |
| 2006/0019064 A1 | 1/2006 | McDonald |
| 2006/0019564 A1 | 1/2006 | Panandiker et al. |
| 2006/0025739 A1 | 2/2006 | DiPalma et al. |
| 2006/0026783 A1 | 2/2006 | McKay |
| 2006/0029739 A1 | 2/2006 | Eden et al. |
| 2006/0030632 A1 | 2/2006 | Krueger et al. |
| 2006/0030661 A1 | 2/2006 | Calhoun et al. |
| 2006/0036228 A1 | 2/2006 | Noda et al. |
| 2006/0037165 A1 | 2/2006 | McDevitt et al. |
| 2006/0037724 A1 | 2/2006 | Akai et al. |
| 2006/0042049 A1 | 3/2006 | Petersen |
| 2006/0046593 A1 | 3/2006 | Senellart et al. |
| 2006/0046599 A1 | 3/2006 | Cerbini et al. |
| 2006/0051266 A1 | 3/2006 | Green et al. |
| 2006/0051387 A1 | 3/2006 | Green |
| 2006/0056756 A1 | 3/2006 | Rosenfeld et al. |
| 2006/0057375 A1 | 3/2006 | Harren et al. |
| 2006/0058207 A1 | 3/2006 | Shaw et al. |
| 2006/0058746 A1 | 3/2006 | Poccia et al. |
| 2006/0058747 A1 | 3/2006 | Rosenfeld et al. |
| 2006/0058748 A1 | 3/2006 | Rosenfeld et al. |
| 2006/0058749 A1 | 3/2006 | Rosenfeld et al. |
| 2006/0058751 A1 | 3/2006 | Rosenfeld et al. |
| 2006/0058752 A1 | 3/2006 | Rosenfeld et al. |
| 2006/0058753 A1 | 3/2006 | Rosenfeld et al. |
| 2006/0058754 A1 | 3/2006 | Rosenfeld et al. |
| 2006/0058755 A1 | 3/2006 | Rosenfeld et al. |
| 2006/0058757 A1 | 3/2006 | Rosenfeld et al. |
| 2006/0058758 A1 | 3/2006 | Rosenfeld et al. |
| 2006/0058759 A1 | 3/2006 | Rosenfeld et al. |
| 2006/0058760 A1 | 3/2006 | Rosenfeld et al. |
| 2006/0058762 A1 | 3/2006 | Yang et al. |
| 2006/0058764 A1 | 3/2006 | Bohlen et al. |
| 2006/0058770 A1 | 3/2006 | Bohlen et al. |
| 2006/0067962 A1 | 3/2006 | Krzysik et al. |
| 2006/0068675 A1 | 3/2006 | Handermann et al. |
| 2006/0069380 A1 | 3/2006 | Chen et al. |
| 2006/0093788 A1 | 5/2006 | Behm et al. |
| 2006/0111684 A1 | 5/2006 | Berba et al. |
| 2006/0116656 A1 | 6/2006 | Hendren et al. |
| 2006/0121097 A1 | 6/2006 | Lodge et al. |
| 2006/0121099 A1 | 6/2006 | Solarek |
| 2006/0124247 A1 | 6/2006 | Collins et al. |
| 2006/0128240 A1 | 6/2006 | Policicchio et al. |
| 2006/0128247 A1 | 6/2006 | Skoog et al. |
| 2006/0128248 A1 | 6/2006 | Ellis |
| 2006/0128585 A1 | 6/2006 | Adair et al. |
| 2006/0133884 A1 | 6/2006 | Oberstadt et al. |
| 2006/0134386 A1 | 6/2006 | Brennan |
| 2006/0135018 A1 | 6/2006 | Brennan |
| 2006/0135926 A1 | 6/2006 | Dick et al. |
| 2006/0135927 A1 | 6/2006 | Zander et al. |
| 2006/0135932 A1 | 6/2006 | Abuto et al. |
| 2006/0137069 A1 | 6/2006 | Yang et al. |
| 2006/0137070 A1 | 6/2006 | Yang et al. |
| 2006/0137842 A1 | 6/2006 | Garnier et al. |
| 2006/0140924 A1 | 6/2006 | Schroeder et al. |
| 2006/0141014 A1 | 6/2006 | Eknoian et al. |
| 2006/0142720 A1 | 6/2006 | Zander et al. |
| 2006/0142721 A1 | 6/2006 | Price |
| 2006/0143767 A1 | 7/2006 | Yang et al. |
| 2006/0143847 A1 | 7/2006 | Vinson et al. |
| 2006/0144024 A1 | 7/2006 | Sauer et al. |
| 2006/0147505 A1 | 7/2006 | Tanzer et al. |
| 2006/0148359 A1 | 7/2006 | Van Gompel et al. |
| 2006/0151518 A1 | 7/2006 | Sarbo et al. |
| 2006/0154547 A1 | 7/2006 | Hurley et al. |
| 2006/0154548 A1 | 7/2006 | Sheehan et al. |
| 2006/0154834 A1 | 7/2006 | Hauser et al. |
| 2006/0159924 A1 | 7/2006 | Hauser et al. |
| 2006/0161125 A1 | 7/2006 | Bohlen et al. |
| 2006/0171997 A1 | 8/2006 | Gruenbacher et al. |
| 2006/0180596 A1 | 8/2006 | Young et al. |
| 2006/0184146 A1 | 8/2006 | Suzuki |
| 2006/0185134 A1 | 8/2006 | Carter et al. |
| 2006/0186131 A1 | 8/2006 | Panning |
| 2006/0186132 A1 | 8/2006 | Panning et al. |
| 2006/0188551 A1 | 8/2006 | Hauser et al. |
| 2006/0200108 A1 | 9/2006 | Mizutani et al. |
| 2006/0210517 A1 | 9/2006 | Mower |
| 2006/0222686 A1 | 10/2006 | Hauser et al. |
| 2006/0224133 A1 | 10/2006 | Gannon et al. |
| 2006/0224134 A1 | 10/2006 | Luizzi et al. |
| 2006/0228971 A1 | 10/2006 | Bridges |
| 2006/0233866 A1 | 10/2006 | Hauser et al. |
| 2006/0234586 A1 | 10/2006 | Wong et al. |
| 2006/0234588 A1 | 10/2006 | Bais |
| 2006/0241554 A1 | 10/2006 | Elder et al. |

(56) References Cited

U.S. PATENT DOCUMENTS

| | | |
|---|---|---|
| 2006/0242780 A1 | 11/2006 | Yang et al. |
| 2006/0243367 A1 | 11/2006 | Engelbart et al. |
| 2006/0243378 A1 | 11/2006 | Alberts |
| 2006/0246256 A1 | 11/2006 | Ausen et al. |
| 2006/0247590 A1 | 11/2006 | Ito et al. |
| 2006/0247599 A1 | 11/2006 | Mullen et al. |
| 2006/0251464 A1 | 11/2006 | Bauer et al. |
| 2006/0251609 A1 | 11/2006 | Sojka et al. |
| 2006/0252876 A1 | 11/2006 | Farawaha et al. |
| 2006/0252877 A1 | 11/2006 | Farawaha et al. |
| 2006/0253078 A1 | 11/2006 | Wu et al. |
| 2006/0265822 A1 | 11/2006 | McKay |
| 2006/0287636 A1 | 12/2006 | Sakai et al. |
| 2006/0290517 A1 | 12/2006 | Cohen et al. |
| 2006/0293205 A1 | 12/2006 | Chung |
| 2007/0000064 A1 | 1/2007 | Li |
| 2007/0009708 A1 | 1/2007 | Dorsey et al. |
| 2007/0010155 A1 | 1/2007 | Branham et al. |
| 2007/0010156 A1 | 1/2007 | Strandqvist |
| 2007/0014947 A1 | 1/2007 | Mengel et al. |
| 2007/0015423 A1 | 1/2007 | Jones et al. |
| 2007/0017075 A1 | 1/2007 | Nguyen |
| 2007/0018364 A1 | 1/2007 | Riviere |
| 2007/0020440 A1 | 1/2007 | Wong et al. |
| 2007/0025797 A1 | 2/2007 | Keck |
| 2007/0026228 A1 | 2/2007 | Hartmann et al. |
| 2007/0028344 A1 | 2/2007 | Czajka |
| 2007/0028808 A1 | 2/2007 | Cook et al. |
| 2007/0032151 A1 | 2/2007 | Ellis |
| 2007/0032769 A1 | 2/2007 | Cohen et al. |
| 2007/0036845 A1 | 2/2007 | Peresefeld et al. |
| 2007/0044903 A1 | 3/2007 | Wisneski et al. |
| 2007/0045135 A1 | 3/2007 | Berger Sharp et al. |
| 2007/0045144 A1 | 3/2007 | Wheeler et al. |
| 2007/0048062 A1 | 3/2007 | Brunner et al. |
| 2007/0048345 A1 | 3/2007 | Huang et al. |
| 2007/0049169 A1 | 3/2007 | Vaidya et al. |
| 2007/0049892 A1 | 3/2007 | Lord et al. |
| 2007/0049894 A1 | 3/2007 | Fitts, Jr. et al. |
| 2007/0059496 A1 | 3/2007 | Russell et al. |
| 2007/0060862 A1 | 3/2007 | Sun et al. |
| 2007/0062968 A1 | 3/2007 | Mark et al. |
| 2007/0073255 A1 | 3/2007 | Thomas et al. |
| 2007/0078423 A1 | 4/2007 | Yamaki et al. |
| 2007/0083018 A1 | 4/2007 | Liu et al. |
| 2007/0090014 A1 | 4/2007 | Wheeler et al. |
| 2007/0092398 A1 | 4/2007 | McDonald |
| 2007/0093164 A1 | 4/2007 | Nakaoka |
| 2007/0093773 A1 | 4/2007 | Tokura et al. |
| 2007/0093882 A1 | 4/2007 | Anderson et al. |
| 2007/0093883 A1 | 4/2007 | Anderson et al. |
| 2007/0093884 A1 | 4/2007 | Anderson et al. |
| 2007/0093885 A1 | 4/2007 | Anderson et al. |
| 2007/0094827 A1 | 5/2007 | Kilkenny et al. |
| 2007/0098953 A1 | 5/2007 | Stabelfeldt et al. |
| 2007/0099531 A1 | 5/2007 | Efremova et al. |
| 2007/0099812 A1 | 5/2007 | Luizzi et al. |
| 2007/0099813 A1 | 5/2007 | Luizzi et al. |
| 2007/0100313 A1 | 5/2007 | Luizzi |
| 2007/0104806 A1 | 5/2007 | Seiberg et al. |
| 2007/0107862 A1 | 5/2007 | West et al. |
| 2007/0113859 A1 | 5/2007 | Allen et al. |
| 2007/0116928 A1 | 5/2007 | Monnerie et al. |
| 2007/0119032 A1 | 5/2007 | Efremova et al. |
| 2007/0123131 A1 | 5/2007 | Nguyen et al. |
| 2007/0130713 A1 | 6/2007 | Chen et al. |
| 2007/0130891 A1 | 6/2007 | Long et al. |
| 2007/0134048 A1 | 6/2007 | Bauer et al. |
| 2007/0134337 A1 | 6/2007 | Villanueva et al. |
| 2007/0135788 A1 | 6/2007 | Damay et al. |
| 2007/0137811 A1 | 6/2007 | Runge et al. |
| 2007/0141130 A1 | 6/2007 | Villanueva et al. |
| 2007/0141930 A1 | 6/2007 | Thomas et al. |
| 2007/0141936 A1 | 6/2007 | Bunyard et al. |
| 2007/0144697 A1 | 6/2007 | Dyer et al. |
| 2007/0147942 A1 | 6/2007 | Sojka et al. |
| 2007/0148432 A1 | 6/2007 | Baker et al. |
| 2007/0151029 A1 | 7/2007 | Bridges |
| 2007/0151052 A1 | 7/2007 | McKay |
| 2007/0151053 A1 | 7/2007 | McKay |
| 2007/0156504 A1 | 7/2007 | Myers et al. |
| 2007/0172610 A1 | 7/2007 | Williams |
| 2007/0172628 A1 | 7/2007 | Seth et al. |
| 2007/0173594 A1 | 7/2007 | Farwaha et al. |
| 2007/0178795 A1 | 8/2007 | Stralin et al. |
| 2007/0179463 A1 | 8/2007 | Takahashi et al. |
| 2007/0179466 A1 | 8/2007 | Tremblay et al. |
| 2007/0191252 A1 | 8/2007 | Kilkenny et al. |
| 2007/0191253 A1 | 8/2007 | Kilkenny et al. |
| 2007/0199165 A1 | 8/2007 | Sun et al. |
| 2007/0202764 A1 | 8/2007 | Marin et al. |
| 2007/0202766 A1 | 8/2007 | Ouellette et al. |
| 2007/0212520 A1 | 9/2007 | Furumori et al. |
| 2007/0212960 A1 | 9/2007 | Walton et al. |
| 2007/0250024 A1 | 10/2007 | Mitchell et al. |
| 2007/0254543 A1 | 11/2007 | Bunyard et al. |
| 2007/0256247 A1 | 11/2007 | Privitera et al. |
| 2007/0264520 A1 | 11/2007 | Wood et al. |
| 2007/0276349 A1 | 11/2007 | Mori et al. |
| 2007/0284069 A1 | 12/2007 | Dyer et al. |
| 2007/0287008 A1 | 12/2007 | Hartmann et al. |
| 2007/0287973 A1 | 12/2007 | Cohen et al. |
| 2007/0293841 A1 | 12/2007 | Sasayama |
| 2007/0295464 A1 | 12/2007 | Fetner et al. |
| 2007/0295465 A1 | 12/2007 | Dyer et al. |
| 2007/0295744 A1 | 12/2007 | Sarbo et al. |
| 2007/0299410 A1 | 12/2007 | Eknoian et al. |
| 2007/0299413 A1 | 12/2007 | Bissah et al. |
| 2007/0299416 A1 | 12/2007 | Noda et al. |
| 2008/0000598 A1 | 1/2008 | Dyer et al. |
| 2008/0000602 A1 | 1/2008 | Dyer et al. |
| 2008/0003906 A1 | 1/2008 | Hill et al. |
| 2008/0014817 A1 | 1/2008 | Zafiroglu et al. |
| 2008/0014818 A1 | 1/2008 | Privitera et al. |
| 2008/0015535 A1 | 1/2008 | Gannon et al. |
| 2008/0022940 A1 | 1/2008 | Kirsch et al. |
| 2008/0029039 A1 | 2/2008 | Jenkins |
| 2008/0032611 A1 | 2/2008 | Dilyard |
| 2008/0041543 A1 | 2/2008 | Dyer et al. |
| 2008/0044628 A1 | 2/2008 | Noda et al. |
| 2008/0044644 A1 | 2/2008 | Luu et al. |
| 2008/0045107 A1 | 2/2008 | Michalon et al. |
| 2008/0046189 A1 | 2/2008 | Allende-Blanco et al. |
| 2008/0046202 A1 | 2/2008 | Allende-Blanco et al. |
| 2008/0051539 A1 | 2/2008 | Kelly |
| 2008/0054519 A1 | 3/2008 | McDonald et al. |
| 2008/0057309 A1 | 3/2008 | Liu et al. |
| 2008/0058744 A1 | 3/2008 | Tippey et al. |
| 2008/0073045 A1 | 3/2008 | Dyer et al. |
| 2008/0073046 A1 | 3/2008 | Dyer et al. |
| 2008/0075760 A1 | 3/2008 | Suzuki et al. |
| 2008/0076315 A1 | 3/2008 | McCormack et al. |
| 2008/0077104 A1 | 3/2008 | Baer et al. |
| 2008/0083772 A1 | 4/2008 | Sellars et al. |
| 2008/0091157 A1 | 4/2008 | Yang |
| 2008/0091158 A1 | 4/2008 | Yang |
| 2008/0095978 A1 | 4/2008 | Siqueira et al. |
| 2008/0097036 A1 | 4/2008 | Blenke et al. |
| 2008/0098547 A1 | 5/2008 | McKey |
| 2008/0102722 A1 | 5/2008 | Borysewicz et al. |
| 2008/0103465 A1 | 5/2008 | Borysewicz et al. |
| 2008/0115302 A1 | 5/2008 | Kilkenny et al. |
| 2008/0014684 A1 | 6/2008 | Sirovatka et al. |
| 2008/0127994 A1 | 6/2008 | Rippl et al. |
| 2008/0132866 A1 | 6/2008 | Siqueira et al. |
| 2008/0138373 A1 | 6/2008 | Liu et al. |
| 2008/0138574 A1 | 6/2008 | Maschino et al. |
| 2008/0145267 A1 | 6/2008 | Do et al. |
| 2008/0145664 A1 | 6/2008 | Sirovatka et al. |
| 2008/0147027 A1 | 6/2008 | Sanabria et al. |
| 2008/0147152 A1 | 6/2008 | Quincy et al. |
| 2008/0148946 A1 | 6/2008 | Lotgerink-Bruinenberg |
| 2008/0149504 A1 | 6/2008 | Benjamin et al. |
| 2008/0171683 A1 | 7/2008 | Johnson et al. |

(56) References Cited

U.S. PATENT DOCUMENTS

| | | |
|---|---|---|
| 2008/0176474 A1 | 7/2008 | Brennan |
| 2008/0177361 A1 | 7/2008 | Anderson |
| 2008/0179027 A1 | 7/2008 | Fish et al. |
| 2008/0182104 A1 | 7/2008 | Fish et al. |
| 2008/0199655 A1 | 8/2008 | Monnerie et al. |
| 2008/0202490 A1 | 8/2008 | Dodo |
| 2008/0206529 A1 | 8/2008 | Ueminami et al. |
| 2008/0208153 A1 | 8/2008 | Oetjen et al. |
| 2008/0208154 A1 | 8/2008 | Oetjen et al. |
| 2008/0216977 A1 | 9/2008 | Dyer et al. |
| 2008/0233382 A1 | 9/2008 | Simmons et al. |
| 2008/0241201 A1 | 10/2008 | Warr et al. |
| 2008/0241511 A1 | 10/2008 | Sandford et al. |
| 2008/0242524 A1 | 10/2008 | Dilyard et al. |
| 2008/0242794 A1 | 10/2008 | Sandford et al. |
| 2008/0248239 A1 | 10/2008 | Pomeroy et al. |
| 2008/0251027 A1 | 10/2008 | Kirsch et al. |
| 2008/0258341 A1 | 10/2008 | Parkes et al. |
| 2008/0268205 A1 | 10/2008 | Vogel et al. |
| 2008/0269703 A1 | 10/2008 | Collins et al. |
| 2008/0274147 A1 | 11/2008 | Schaeffer et al. |
| 2008/0289762 A1 | 11/2008 | Blenke et al. |
| 2008/0299061 A1 | 12/2008 | Nam |
| 2008/0300562 A1 | 12/2008 | Ahoniemi et al. |
| 2008/0300565 A1 | 12/2008 | Takahashi et al. |
| 2008/0300568 A1 | 12/2008 | Fujioka et al. |
| 2008/0312627 A1 | 12/2008 | Takeuchi et al. |
| 2008/0318004 A1 | 12/2008 | Ruhe et al. |
| 2008/0319408 A1 | 12/2008 | Uchimoto et al. |
| 2009/0004494 A1 | 1/2009 | Blenke et al. |
| 2009/0019825 A1 | 1/2009 | Skirius et al. |
| 2009/0020139 A1* | 1/2009 | Sumnicht ............... D21H 13/08 134/6 |
| 2009/0029619 A1* | 1/2009 | Kovalainen ............ D04H 1/425 442/334 |
| 2009/0029620 A1 | 1/2009 | Miura |
| 2009/0032636 A1 | 2/2009 | Orlandi et al. |
| 2009/0036858 A1 | 2/2009 | Van Den Bogart et al. |
| 2009/0044811 A1 | 2/2009 | Welchel et al. |
| 2009/0044812 A1 | 2/2009 | Welchel et al. |
| 2009/0048571 A1 | 2/2009 | Catalan et al. |
| 2009/0054862 A1 | 2/2009 | Tatsukawa |
| 2009/0054864 A1 | 2/2009 | Lira et al. |
| 2009/0056091 A1 | 3/2009 | Jezzi |
| 2009/0062172 A1 | 3/2009 | Cunningham et al. |
| 2009/0062762 A1 | 3/2009 | Himbergen et al. |
| 2009/0065436 A1 | 3/2009 | Kalayci et al. |
| 2009/0069771 A1 | 3/2009 | Yu et al. |
| 2009/0069780 A1 | 3/2009 | Plentovich et al. |
| 2009/0075546 A1 | 3/2009 | Barnholtz et al. |
| 2009/0082744 A1 | 3/2009 | Hakansson et al. |
| 2009/0087465 A1 | 4/2009 | Doney et al. |
| 2009/0088359 A1 | 4/2009 | Denton |
| 2009/0090736 A1 | 4/2009 | Cowell et al. |
| 2009/0092809 A1 | 4/2009 | Hurley et al. |
| 2009/0094729 A1 | 4/2009 | Lin et al. |
| 2009/0101163 A1 | 4/2009 | Brunner |
| 2009/0101751 A1 | 4/2009 | Cittadino et al. |
| 2009/0112283 A1 | 4/2009 | Kriksunov et al. |
| 2009/0114669 A1 | 5/2009 | Decker et al. |
| 2009/0117174 A1 | 5/2009 | Cunningham et al. |
| 2009/0118152 A1 | 5/2009 | Lam et al. |
| 2009/0123707 A1 | 5/2009 | Skoog et al. |
| 2009/0126074 A1 | 5/2009 | Mattesky |
| 2009/0126885 A1 | 5/2009 | Akai et al. |
| 2009/0131890 A1 | 5/2009 | Rourke et al. |
| 2009/0131896 A1 | 5/2009 | Ebitsuka et al. |
| 2009/0133206 A1 | 5/2009 | Benjamin et al. |
| 2009/0144913 A1 | 6/2009 | Yu et al. |
| 2009/0145936 A1 | 6/2009 | Convents et al. |
| 2009/0148596 A1 | 6/2009 | Carrol et al. |
| 2009/0148933 A1 | 6/2009 | Battrell et al. |
| 2009/0151748 A1 | 6/2009 | Ridenhour |
| 2009/0155325 A1 | 6/2009 | Wenzel et al. |
| 2009/0156078 A1 | 6/2009 | Connaughton, I et al. |
| 2009/0156080 A1 | 6/2009 | Finch et al. |
| 2009/0157020 A1 | 6/2009 | Shi et al. |
| 2009/0157022 A1 | 6/2009 | MacDonald et al. |
| 2009/0157032 A1 | 6/2009 | MacDonald et al. |
| 2009/0159598 A1 | 6/2009 | Kuehneman |
| 2009/0162446 A1 | 6/2009 | Gatto et al. |
| 2009/0165228 A1 | 7/2009 | Kilkenny et al. |
| 2009/0169827 A1 | 7/2009 | Dharmadhikary et al. |
| 2009/0170978 A1 | 7/2009 | Kelly |
| 2009/0171309 A1 | 7/2009 | VanDenBogart et al. |
| 2009/0177174 A1 | 7/2009 | Akiyama et al. |
| 2009/0178222 A1 | 7/2009 | Flemister et al. |
| 2009/0181060 A1 | 7/2009 | Rosato et al. |
| 2009/0182296 A1 | 7/2009 | Dennis et al. |
| 2009/0186189 A1 | 7/2009 | White et al. |
| 2009/0189009 A1 | 7/2009 | Rothwell et al. |
| 2009/0194435 A1 | 8/2009 | Heilman et al. |
| 2009/0197041 A1 | 8/2009 | Lake et al. |
| 2009/0198203 A1 | 8/2009 | Lira et al. |
| 2009/0198204 A1 | 8/2009 | Kudo et al. |
| 2009/0199687 A1 | 8/2009 | Bohm et al. |
| 2009/0204090 A1 | 8/2009 | Dennis et al. |
| 2009/0204092 A1 | 8/2009 | Loyd et al. |
| 2009/0204095 A1 | 8/2009 | McDaniel |
| 2009/0205981 A1 | 8/2009 | Daul |
| 2009/0208699 A1 | 8/2009 | Miyauchi et al. |
| 2009/0209156 A1 | 8/2009 | Pedoja |
| 2009/0209927 A1 | 8/2009 | Ito et al. |
| 2009/0209928 A1 | 8/2009 | Ito et al. |
| 2009/0209929 A1 | 8/2009 | Ito et al. |
| 2009/0211594 A1 | 8/2009 | Tojo et al. |
| 2009/0211718 A1 | 8/2009 | Toubeau et al. |
| 2009/0217870 A1 | 9/2009 | Luu |
| 2009/0217882 A1 | 9/2009 | Jenkins |
| 2009/0218719 A1 | 9/2009 | Marin et al. |
| 2009/0227974 A1 | 9/2009 | Glaug et al. |
| 2009/0233073 A1 | 9/2009 | Bornemann et al. |
| 2009/0236464 A1 | 9/2009 | Cittadino et al. |
| 2009/0238849 A1 | 9/2009 | Iwata et al. |
| 2009/0240220 A1 | 9/2009 | MacDonald et al. |
| 2009/0241242 A1 | 10/2009 | Beatty et al. |
| 2009/0241497 A1 | 10/2009 | Imai et al. |
| 2009/0247977 A1 | 10/2009 | Takeuchi et al. |
| 2009/0247978 A1 | 10/2009 | Boissier |
| 2009/0258218 A1 | 10/2009 | Sanford et al. |
| 2009/0258984 A1 | 10/2009 | Sandford et al. |
| 2009/0262597 A1 | 10/2009 | Kieffer et al. |
| 2009/0270824 A1 | 10/2009 | Kapik et al. |
| 2009/0272240 A1 | 11/2009 | Böhm et al. |
| 2009/0272665 A1 | 11/2009 | Cornell |
| 2009/0286437 A1 | 11/2009 | Cunningham et al. |
| 2009/0287171 A1 | 11/2009 | Ito et al. |
| 2009/0287177 A1 | 11/2009 | Tatsukawa et al. |
| 2009/0291147 A1 | 11/2009 | Sandford et al. |
| 2009/0299310 A1 | 12/2009 | Ito et al. |
| 2009/0299312 A1 | 12/2009 | MacDonald et al. |
| 2009/0301912 A1 | 12/2009 | Cornell |
| 2009/0302049 A1 | 12/2009 | Cornell |
| 2009/0302052 A1 | 12/2009 | Cornell |
| 2009/0306614 A1 | 12/2009 | Boissier |
| 2009/0306615 A1 | 12/2009 | Olsson |
| 2009/0308548 A1 | 12/2009 | Tramontina et al. |
| 2009/0312731 A1 | 12/2009 | Steindl et al. |
| 2009/0314793 A1 | 12/2009 | Reedy et al. |
| 2009/0325276 A1 | 12/2009 | Battrell et al. |
| 2009/0326492 A1 | 12/2009 | Hietpas |
| 2009/0326495 A1 | 12/2009 | MacDonald et al. |
| 2010/0004615 A1 | 1/2010 | Boissier |
| 2010/0010462 A1 | 1/2010 | Kurata |
| 2010/0011506 A1 | 1/2010 | Jensen et al. |
| 2010/0024489 A1 | 2/2010 | Lin et al. |
| 2010/0025886 A1 | 2/2010 | Carroll |
| 2010/0031966 A1 | 2/2010 | Allen |
| 2010/0037628 A1 | 2/2010 | Hatanaka et al. |
| 2010/0038818 A1 | 2/2010 | McDonald |
| 2010/0044407 A1 | 2/2010 | Yardley |
| 2010/0048072 A1 | 2/2010 | Kauschke et al. |
| 2010/0048801 A1 | 2/2010 | Calhoun et al. |
| 2010/0056296 A1 | 3/2010 | Kumamoto et al. |

(56) References Cited

U.S. PATENT DOCUMENTS

| | | |
|---|---|---|
| 2010/0057034 A1 | 3/2010 | Dennis et al. |
| 2010/0057147 A1 | 3/2010 | Fassih et al. |
| 2010/0059435 A1 | 3/2010 | Imai et al. |
| 2010/0062671 A1 | 3/2010 | Child et al. |
| 2010/0063466 A1 | 3/2010 | Husmark et al. |
| 2010/0068484 A1 | 3/2010 | Kaufman |
| 2010/0069861 A1 | 3/2010 | Yao et al. |
| 2010/0069865 A1 | 3/2010 | Rosenfeld et al. |
| 2010/0069875 A1 | 3/2010 | Yao et al. |
| 2010/0072227 A1 | 3/2010 | Cittadino et al. |
| 2010/0075120 A1 | 3/2010 | Gustafsson et al. |
| 2010/0081352 A1 | 4/2010 | Westwood |
| 2010/0082088 A1 | 4/2010 | Fassih et al. |
| 2010/0089935 A1 | 4/2010 | Heilman et al. |
| 2010/0100069 A1 | 4/2010 | Nakaoka |
| 2010/0114366 A1 | 5/2010 | Case et al. |
| 2010/0117495 A1 | 5/2010 | Cornell |
| 2010/0121294 A1 | 5/2010 | Okawa et al. |
| 2010/0121303 A1 | 5/2010 | Kudo et al. |
| 2010/0121304 A1 | 5/2010 | Zhou et al. |
| 2010/0131302 A1 | 5/2010 | Hashino et al. |
| 2010/0137072 A1 | 6/2010 | Kumamoto et al. |
| 2010/0137773 A1 | 6/2010 | Gross et al. |
| 2010/0137824 A1 | 6/2010 | Uematsu et al. |
| 2010/0143652 A1 | 6/2010 | Stockton et al. |
| 2010/0143671 A1 | 6/2010 | Brennan |
| 2010/0152306 A1 | 6/2010 | Warr et al. |
| 2010/0152690 A1 | 6/2010 | Ong et al. |
| 2010/0152692 A1 | 6/2010 | Ong et al. |
| 2010/0152693 A1 | 6/2010 | Lira et al. |
| 2010/0158751 A1 | 6/2010 | Friderich et al. |
| 2010/0158752 A1 | 6/2010 | Friderich et al. |
| 2010/0158753 A1 | 6/2010 | Friderich et al. |
| 2010/0159770 A1 | 6/2010 | Walser et al. |
| 2010/0160205 A1 | 6/2010 | Ouellette et al. |
| 2010/0162541 A1 | 7/2010 | Luo |
| 2010/0167029 A1 | 7/2010 | Luo |
| 2010/0173547 A1 | 7/2010 | Katayama et al. |
| 2010/0173568 A1 | 7/2010 | Dilyard et al. |
| 2010/0174260 A1 | 7/2010 | Di Luccio et al. |
| 2010/0179624 A1 | 7/2010 | Anderson et al. |
| 2010/0186931 A1 | 7/2010 | Obara et al. |
| 2010/0198177 A1 | 8/2010 | Yahiaoui et al. |
| 2010/0199435 A1 | 8/2010 | Jensen et al. |
| 2010/0201020 A1 | 8/2010 | Russell et al. |
| 2010/0203291 A1 | 8/2010 | Dyer et al. |
| 2010/0209668 A1 | 8/2010 | Ducker et al. |
| 2010/0212849 A1 | 8/2010 | Smith et al. |
| 2010/0222459 A1 | 9/2010 | Kelly et al. |
| 2010/0222463 A1 | 9/2010 | Brady et al. |
| 2010/0222755 A1 | 9/2010 | Westwood |
| 2010/0222761 A1 | 9/2010 | Westwood et al. |
| 2010/0223715 A1 | 9/2010 | Lyons |
| 2010/0224574 A1 | 9/2010 | Youngs et al. |
| 2010/0226871 A1 | 9/2010 | Fraser et al. |
| 2010/0227138 A1 | 9/2010 | Ouellette |
| 2010/0228204 A1 | 9/2010 | Beatty et al. |
| 2010/0236034 A1 | 9/2010 | Eagles et al. |
| 2010/0236735 A1 | 9/2010 | Goulet et al. |
| 2010/0239814 A1 | 9/2010 | Mourad et al. |
| 2010/0239843 A1 | 9/2010 | Luu et al. |
| 2010/0240569 A1 | 9/2010 | Boutique et al. |
| 2010/0240571 A1 | 9/2010 | Boutique et al. |
| 2010/0249740 A1 | 9/2010 | Miyamoto et al. |
| 2010/0249741 A1 | 9/2010 | Fingal et al. |
| 2010/0251486 A1 | 10/2010 | Yu et al. |
| 2010/0262090 A1 | 10/2010 | Riesinger |
| 2010/0263178 A1 | 10/2010 | Jensen et al. |
| 2010/0266824 A1 | 10/2010 | Westwood et al. |
| 2010/0267914 A1 | 10/2010 | Westwood et al. |
| 2010/0274208 A1 | 10/2010 | Gabrielli et al. |
| 2010/0282621 A1 | 11/2010 | Hatanaka et al. |
| 2010/0286641 A1 | 11/2010 | Yao et al. |
| 2010/0286817 A1 | 11/2010 | Goeking et al. |
| 2010/0286818 A1 | 11/2010 | Goeking et al. |
| 2010/0294980 A1 | 11/2010 | Hartmann et al. |
| 2010/0310810 A1 | 12/2010 | Bond et al. |
| 2010/0310837 A1 | 12/2010 | Bond et al. |
| 2010/0310845 A1 | 12/2010 | Bond et al. |
| 2010/0311296 A1 | 12/2010 | Boehmer et al. |
| 2010/0312208 A1 | 12/2010 | Bond et al. |
| 2010/0312211 A1 | 12/2010 | Bond et al. |
| 2010/0312212 A1 | 12/2010 | Bond et al. |
| 2010/0314195 A1 | 12/2010 | Bliton et al. |
| 2010/0314267 A1 | 12/2010 | Green et al. |
| 2010/0319152 A1 | 12/2010 | Prizepasniak |
| 2010/0319712 A1 | 12/2010 | Czajka |
| 2010/0330140 A1 | 12/2010 | Stewart et al. |
| 2011/0005016 A1 | 1/2011 | Johnson et al. |
| 2011/0015603 A1 | 1/2011 | Sukegawa |
| 2011/0020618 A1 | 1/2011 | Brennan et al. |
| 2011/0027534 A1 | 2/2011 | Ogawa et al. |
| 2011/0028928 A1 | 2/2011 | Takai et al. |
| 2011/0030702 A1 | 2/2011 | Czajka, Jr. et al. |
| 2011/0031263 A1 | 2/2011 | Carrier et al. |
| 2011/0046588 A1 | 2/2011 | Jensen et al. |
| 2011/0057346 A1 | 3/2011 | Nunn |
| 2011/0059329 A1 | 3/2011 | Dobrawa et al. |
| 2011/0066128 A1 | 3/2011 | Takahashi |
| 2011/0066214 A1 | 3/2011 | Anderson et al. |
| 2011/0072967 A1 | 3/2011 | Wood et al. |
| 2011/0076471 A1 | 3/2011 | Takahashi et al. |
| 2011/0077354 A1 | 3/2011 | Stoyanov et al. |
| 2011/0077724 A1 | 3/2011 | Anderson et al. |
| 2011/0082527 A1 | 4/2011 | Anderson et al. |
| 2011/0082528 A1 | 4/2011 | Anderson et al. |
| 2011/0082529 A1 | 4/2011 | Everaerts et al. |
| 2011/0087184 A1 | 4/2011 | Wöhlke et al. |
| 2011/0087185 A1 | 4/2011 | Wöhlke et al. |
| 2011/0092942 A1 | 4/2011 | Ruman et al. |
| 2011/0092943 A1 | 4/2011 | Bishop et al. |
| 2011/0095117 A1 | 4/2011 | Haque et al. |
| 2011/0100574 A1 | 5/2011 | Barnholtz et al. |
| 2011/0110818 A1 | 5/2011 | Mowbray-d'Arbela et al. |
| 2011/0114414 A1 | 5/2011 | Bliton et al. |
| 2011/0118655 A1 | 5/2011 | Fassih et al. |
| 2011/0118687 A1 | 5/2011 | Elder et al. |
| 2011/0119850 A1 | 5/2011 | Mallory et al. |
| 2011/0120486 A1 | 5/2011 | Doney et al. |
| 2011/0123775 A1 | 5/2011 | Westwood |
| 2011/0123802 A1 | 5/2011 | Chang et al. |
| 2011/0124258 A1 | 5/2011 | White et al. |
| 2011/0125117 A1 | 5/2011 | Kudo |
| 2011/0125119 A1 | 5/2011 | Weismantel et al. |
| 2011/0129645 A1 | 6/2011 | Dyer et al. |
| 2011/0130275 A1 | 6/2011 | Weismantel et al. |
| 2011/0130735 A1 | 6/2011 | Weismantel et al. |
| 2011/0138685 A1 | 6/2011 | Kalayci et al. |
| 2011/0143989 A1 | 6/2011 | Petkus et al. |
| 2011/0144604 A1 | 6/2011 | Noda et al. |
| 2011/0144605 A1 | 6/2011 | Noda et al. |
| 2011/0144607 A1 | 6/2011 | Suzuki et al. |
| 2011/0146927 A1 | 6/2011 | Farwaha et al. |
| 2011/0150787 A1 | 6/2011 | Gonzales et al. |
| 2011/0150788 A1 | 6/2011 | Gonzales et al. |
| 2011/0150949 A1 | 6/2011 | Gonzales et al. |
| 2011/0150950 A1 | 6/2011 | Gonzales et al. |
| 2011/0150951 A1 | 6/2011 | Gonzales et al. |
| 2011/0150955 A1 | 6/2011 | Klingman |
| 2011/0151738 A1 | 6/2011 | Moore et al. |
| 2011/0152795 A1 | 6/2011 | Aledo et al. |
| 2011/0152813 A1 | 6/2011 | Ellingson |
| 2011/0159265 A1 | 6/2011 | Hurley et al. |
| 2011/0162989 A1 | 7/2011 | Ducker et al. |
| 2011/0166540 A1 | 7/2011 | Yang |
| 2011/0166542 A1 | 7/2011 | Yao et al. |
| 2011/0172630 A1 | 7/2011 | Nomoto et al. |
| 2011/0174834 A1 | 7/2011 | Case et al. |
| 2011/0178487 A1 | 7/2011 | Noda et al. |
| 2011/0178585 A1 | 7/2011 | Biser |
| 2011/0195314 A1 | 8/2011 | Yu et al. |
| 2011/0203946 A1 | 8/2011 | McCloskey et al. |
| 2011/0207644 A1 | 8/2011 | Doney et al. |
| 2011/0210198 A1 | 9/2011 | Case et al. |

(56) References Cited

U.S. PATENT DOCUMENTS

| | | |
|---|---|---|
| 2011/0217503 A1 | 9/2011 | Flannery |
| 2011/0217539 A1 | 9/2011 | Bonner et al. |
| 2011/0232004 A1 | 9/2011 | Meine et al. |
| 2011/0238026 A1 | 9/2011 | Zhang et al. |
| 2011/0251575 A1 | 10/2011 | Kuroda et al. |
| 2011/0251576 A1 | 10/2011 | Ando et al. |
| 2011/0253829 A1 | 10/2011 | Goeking et al. |
| 2011/0256399 A1 | 10/2011 | Shimotsu et al. |
| 2011/0258791 A1 | 10/2011 | Batchvarova et al. |
| 2011/0258796 A1 | 10/2011 | Batchvarova et al. |
| 2011/0259908 A1 | 10/2011 | Case et al. |
| 2011/0260357 A1 | 10/2011 | Marin et al. |
| 2011/0262371 A1 | 10/2011 | Deleersnyder et al. |
| 2011/0262504 A1 | 10/2011 | Deleersnyder et al. |
| 2011/0262645 A1 | 10/2011 | Batchvarova et al. |
| 2011/0262648 A1 | 10/2011 | Lee et al. |
| 2011/0263757 A1 | 10/2011 | Rand et al. |
| 2011/0265272 A1 | 11/2011 | Hutmacher et al. |
| 2011/0272112 A1 | 11/2011 | Aberg et al. |
| 2011/0276178 A1 | 11/2011 | Petersen et al. |
| 2011/0283458 A1 | 11/2011 | Gillette et al. |
| 2011/0284157 A1 | 11/2011 | Takahashi |
| 2011/0284319 A1 | 11/2011 | Frederick et al. |
| 2011/0288514 A1 | 11/2011 | Kuroda et al. |
| 2011/0288520 A1 | 11/2011 | Brud et al. |
| 2011/0290437 A1 | 12/2011 | Vogel et al. |
| 2011/0293931 A1 | 12/2011 | Vogel et al. |
| 2011/0300380 A1 | 12/2011 | Brady |
| 2011/0303699 A1 | 12/2011 | Cittadino et al. |
| 2011/0306726 A1 | 12/2011 | Bailey et al. |
| 2011/0308051 A1 | 12/2011 | Lin et al. |
| 2011/0309097 A1 | 12/2011 | Heilman et al. |
| 2011/0313384 A1 | 12/2011 | Akiyama |
| 2012/0001014 A1 | 1/2012 | Decker |
| 2012/0003432 A1 | 1/2012 | O'Donnell et al. |
| 2012/0004634 A1 | 1/2012 | Fujioka et al. |
| 2012/0016330 A1 | 1/2012 | Plentovich et al. |
| 2012/0022487 A1 | 1/2012 | Akiyama |
| 2012/0029453 A1 | 2/2012 | Noda et al. |
| 2012/0037746 A1 | 2/2012 | Cittadino et al. |
| 2012/0045639 A1 | 2/2012 | Whitmore et al. |
| 2012/0046633 A1 | 2/2012 | Okswa et al. |
| 2012/0053547 A1 | 3/2012 | Schroeder et al. |
| 2012/0053550 A1 | 3/2012 | Kinoshita et al. |
| 2012/0055922 A1 | 3/2012 | Aksan et al. |
| 2012/0060258 A1 | 3/2012 | Stewart et al. |
| 2012/0065603 A1 | 3/2012 | Elder et al. |
| 2012/0066851 A1 | 3/2012 | Gonzales et al. |
| 2012/0070479 A1 | 3/2012 | Doney et al. |
| 2012/0070480 A1 | 3/2012 | Amos et al. |
| 2012/0071378 A1 | 3/2012 | Gonzales et al. |
| 2012/0071379 A1 | 3/2012 | Gonzales et al. |
| 2012/0071380 A1 | 3/2012 | Gonzales et al. |
| 2012/0071848 A1 | 3/2012 | Zhang et al. |
| 2012/0073030 A1 | 3/2012 | Beatty et al. |
| 2012/0076845 A1 | 3/2012 | Doney et al. |
| 2012/0077007 A1 | 3/2012 | McDonald et al. |
| 2012/0089106 A1 | 4/2012 | Komatsu et al. |
| 2012/0089107 A1 | 4/2012 | Vandenbogart et al. |
| 2012/0089155 A1 | 4/2012 | Otsuka et al. |
| 2012/0090112 A1 | 4/2012 | Carrier et al. |
| 2012/0090113 A1 | 4/2012 | Manifold et al. |
| 2012/0090119 A1 | 4/2012 | Carrier et al. |
| 2012/0095424 A1 | 4/2012 | Komatsu et al. |
| 2012/0097175 A1 | 4/2012 | Allen et al. |
| 2012/0100350 A1 | 4/2012 | Shim |
| 2012/0103893 A1 | 5/2012 | Youngs et al. |
| 2012/0108421 A1 | 5/2012 | Akiyama et al. |
| 2012/0109091 A1 | 5/2012 | Akiyama et al. |
| 2012/0109092 A1 | 5/2012 | Austin et al. |
| 2012/0111519 A1 | 5/2012 | Toubeau et al. |
| 2012/0115718 A1 | 5/2012 | Nakashita et al. |
| 2012/0116338 A1 | 5/2012 | Ferry et al. |
| 2012/0121671 A1 | 5/2012 | Goldstein |
| 2012/0125533 A1 | 5/2012 | Takahashi et al. |
| 2012/0125552 A1 | 5/2012 | Goulet et al. |
| 2012/0133213 A1 | 5/2012 | Borke et al. |
| 2012/0137459 A1 | 6/2012 | Privitera et al. |
| 2012/0141568 A1 | 6/2012 | Privitera et al. |
| 2012/0143166 A1 | 6/2012 | Kimura et al. |
| 2012/0144611 A1 | 6/2012 | Baker et al. |
| 2012/0148821 A1 | 6/2012 | Ducker et al. |
| 2012/0150136 A1 | 6/2012 | Ueminami et al. |
| 2012/0157949 A1 | 6/2012 | Knight et al. |
| 2012/0157952 A1 | 6/2012 | Poruthoor et al. |
| 2012/0160400 A1 | 6/2012 | Calewarts et al. |
| 2012/0160436 A1 | 6/2012 | Zwick et al. |
| 2012/0160715 A1 | 6/2012 | Muvundamina et al. |
| 2012/0164200 A1 | 6/2012 | Qin et al. |
| 2012/0165773 A1 | 6/2012 | Nakashita et al. |
| 2012/0171155 A1 | 7/2012 | Cunningham et al. |
| 2012/0171267 A1 | 7/2012 | Cunningham |
| 2012/0171300 A1 | 7/2012 | Koenig et al. |
| 2012/0171301 A1 | 7/2012 | Koenig et al. |
| 2012/0175073 A1 | 7/2012 | Nonni et al. |
| 2012/0177888 A1 | 7/2012 | Escafere et al. |
| 2012/0178326 A1 | 7/2012 | Terrell |
| 2012/0183772 A1 | 7/2012 | Nonni et al. |
| 2012/0184935 A1 | 7/2012 | Suzuki |
| 2012/0191055 A1 | 7/2012 | Nozaki et al. |
| 2012/0191056 A1 | 7/2012 | Nozaki et al. |
| 2012/0199267 A1 | 8/2012 | Popp et al. |
| 2012/0199268 A1 | 8/2012 | Popp et al. |
| 2012/0199301 A1 | 8/2012 | Strandqvist |
| 2012/0201770 A1 | 8/2012 | Frentzko et al. |
| 2012/0203191 A1 | 8/2012 | Maruo et al. |
| 2012/0204905 A1 | 8/2012 | Chou |
| 2012/0207871 A1 | 8/2012 | Yamamoto |
| 2012/0214373 A1 | 8/2012 | Calewarts et al. |
| 2012/0215195 A1 | 8/2012 | Lira et al. |
| 2012/0216329 A1 | 8/2012 | Dennis |
| 2012/0220971 A1 | 8/2012 | Harada et al. |
| 2012/0222687 A1 | 9/2012 | Czajka, Jr. et al. |
| 2012/0225601 A1 | 9/2012 | Westwood |
| 2012/0225773 A1 | 9/2012 | Krueger et al. |
| 2012/0225966 A1 | 9/2012 | Shi et al. |
| 2012/0227183 A1 | 9/2012 | Muskelly |
| 2012/0227203 A1 | 9/2012 | Ouellette et al. |
| 2012/0231059 A1 | 9/2012 | Schmitz et al. |
| 2012/0232510 A1 | 9/2012 | Greco et al. |
| 2014/0141677 A1 | 5/2014 | Tai et al. |

FOREIGN PATENT DOCUMENTS

| | | | |
|---|---|---|---|
| EP | 1 302 592 A1 | | 4/2003 |
| EP | 2 196 579 A1 | | 6/2010 |
| JP | 1-97300 A | | 4/1989 |
| JP | 1-193055 A | | 8/1989 |
| JP | 10-310960 | | 11/1998 |
| JP | 10310960 A | * | 11/1998 |
| JP | 11093055 A | * | 4/1999 |
| JP | 2005-500441 A | | 1/2005 |
| WO | WO 02/50356 A1 | | 6/2002 |

OTHER PUBLICATIONS

Office Action dated Mar. 9, 2017 in Eurasian Patent Application No. 201591110/31 (with English translation).

Japanese Office Action dated Apr. 11, 2017 in Patent Application No. 2015-547925 (with English translation).

International Search Report and Written Opinion dated Dec. 19, 2013 in PCT/US13/53756.

N. Mao, et al. "A framework for determining the bonding intensity in hydroentangled nonwoven frabrics" Composites Science and Technology, Vo. 66, 2006, pp. 80-91.

Office Action dated Sep. 1, 2015 in Colombian Patent Application No. 15-156.915 (with English language translation).

Combined Chinese Office Action and Search Report dated May 5, 2016 in Patent Application No. 201380069791.7 (with English language translation).

Search Report dated Apr. 13, 2017 in Chilean Patent Application No. 201501626 (with English translation of categories of cited documents).

(56) References Cited

OTHER PUBLICATIONS

Office Action dated May 3, 2017 in European Patent Application No. 13 863 644.4.
Chinese Office Action dated Jan. 5, 2017 in Patent Application No. 201380069791.7 (with English language translation).
European Office Action dated Feb. 7, 2018 in European Patent Application No. 13 863 644.4.
Office Action dated Sep. 19, 2017 in Eurasian Patent Application No. 201591110/31 (with English translation).
Office Action dated Feb. 13, 2018 in Israeli Patent Application No. 239392.
Mexican Office Action dated Nov. 22, 2017 in Patent Application No. MX/a/2015/007588.
New Zealand Office Action dated Jul. 11, 2018 in New Zealand Patent Application No. 708910, 4 pages.
Office Action dated Jun. 1, 2018 in Mexican Patent Application No. MX/a/2015/007588.
New Zealand Office Action dated Jan. 28, 2019 in New Zealand Patent Application No. 708910, 2 pages.
Office Action (Requisition By The Examiner) dated Jun. 21, 2019 in Canadian Patent Application No. 2,894,674.
Korean Office Action dated Jun. 20, 2019 in Korean Patent Application No. 10-2015-7015636 (with English translation), 15 pages.
Office Action issued in Canadian Patent Application No. 2,894,674 filed Aug. 6, 2013.
Brazilian Office Action dated Feb. 12, 2021 in Brazilian Patent Application No. BR 112015013767-9, 3 pages.
Grant Decision dated Jul. 8, 2020, in European Patent Application No. 13 863 644.4.

\* cited by examiner

| Trial Number | Material | BW (g/m²) | MD TS (N.5 cm) | MD Elong@Max (%) | CD TS (N.5 cm) | CD Elong@Max (%) | Thickness @ 0.5 kPa (mm) |
|---|---|---|---|---|---|---|---|
| | | | WET | WET | WET | WET | |
| A | Suouminen Dispersible | 70 | 7.916 | 20.76 | 6.516 | 50.83 | 0.64 |
| B | Buckeye Dispersible | 75 | 5.18 | 10.43 | 3.306 | 17.07 | 0.66 |
| C | KC Cottonelle Dispersible | 80 | 8.593 | 18.82 | 6.554 | 26.06 | 0.55 |
| D | JHI Dispersible | 47.5 | 11.6 | 30.4 | 5.9 | 37.95 | 0.8 |
| E | JHI Non-Dispersible | 50.5 | 14.5 | 52 | 14.8 | 50.1 | 0.54 |
| F | KC Huggies Baby Wipe | 70 | 10.54 | 32 | 8.8 | 20.18 | 0.9 |
| H | Clorox Cleaning Wipes | 51 | 33 | 21 | 18 | 30 | 0.51 |

Fig. 2

HYDROENTANGLED AIRLAID WEB AND PRODUCTS OBTAINED THEREFROM

CROSS REFERENCE TO RELATED APPLICATIONS

This application is a divisional application of prior U.S. application Ser. No. 13/943,146, filed July 16, 2013, the disclosure of which is incorporated herein by reference in its entirety. The parent application claims priority to U.S. Provisional Application No. 61/736,837, filed Dec. 13, 2012, the disclosure of which is incorporated herein by reference in its entirety.

FIELD OF THE INVENTION

This invention is directed to a continuous method for preparing disposable nonwoven webs which employs a minimal number of operations and provides an economical product which is useful as a flushable or disposable article such as a disposable wipe or wipers.

BACKGROUND OF THE INVENTION

Disposable nonwoven substrates are employed for the production of a wide variety of consumer products which are generally used once and discarded. Such products include disposable cleansing wipes, disposable diapers, disposable adult incontinence products, disposable pads typically employed in hospitals for absorption of body fluids and cosmetic applicators or cosmetic pads for removal of make-up and other materials from a keratinous substrate.

Such commercial products constitute an industry having ever increasing growth potential and expansion of utility. However, as virtually all such products potentially enter the environment through landfill or sewage systems, there is a need for a disposable nonwoven material that is simple to produce, contains a minimal or no amount of chemical components that have poor biodegradeability such as binders, adhesives or thermoplastic polymers and yet has good wet tensile strength as required for performance. In addition, a product is sought which is constructed to have minimal lint content and meets codes for categorizing as a flushable article acceptable for municipal and private sewage systems, while being economical to produce.

Conventionally, nonwoven disposable wipe products can be produced via one of two basic technologies known in the industry as "airlace" and "hydraspun" processes. Different producers may conduct these technologies with variation based on intended end use and available production equipment but the basic principles of operation are retained.

Airlace methods combine the operations of depositing an airlaid web of staple length fibers and wood pulp fibers onto a nonwoven carrier layer or precursor base nonwoven web and hydroentangling the airlaid layer with the nonwoven carrier. This technology is described in U.S. Pat. No. 8,250,719 to Ouellette and the references described therein. In addition to employing a carrier web, Ouellette describes bonding the airlaid fibers with hot air or a spray adhesive.

According to the "hydraspun" method as described in U.S. Pat. No. 4,755,421 to Manning et al. a wetlaid web of pulp and manmade fibers is hydroentangled and dried. However, U.S. Pat. No. 5,292,581 to Viazmensky et al. indicates that such products suffer from poor wet strength and describe that the addition of binders substantially improves the strength. More recently, U.S. Pat. No. 7,732,357 to Annis et al. describes the use of binder fibers to the nonwoven sheet that upon heating become activated by at least partial melting and form fiber to fiber bonds. The binder fibers contain polyethylene, polypropylene, polyethylene terephthalate and mixtures thereof.

Therefore, there remains a need for a method to prepare a nonwoven web that contains no adhesive, binder or binder fibers, is convenient and economical to conduct and provides a dispersible nonwoven web having good performance strength, yet being acceptable as a flushable product for municipal sewer and private septic systems.

SUMMARY OF THE INVENTION

Thus, an objective of the present invention is to provide a method to produce a nonwoven web that includes minimal processing operations, does not use adhesives, binders or binding fibers and provides a nonwoven web having sufficient wet tensile strength for use as a wipe. Another objective of this invention is to provide a nonwoven web having sufficient wet strength to be employed as a wipe that is acceptable for disposal in sewer and septic systems.

These and other objectives have been achieved according to the present invention, the first embodiment of which includes a method for production of a nonwoven web, comprising: preparing a mixture of natural cellulose fibers and staple fibers; airforming the mixture to obtain at least one homogeneous airlaid web; hydroentangling the airlaid web to consolidate the web on at least one side; and drying the hydroentangled web to obtain the nonwoven web; wherein the airforming and hydroentangling are conducted in a continuous operation, a content of the natural cellulose fibers in the mixture of fibers is no less than 50% by weight and a content of the staple fibers is no more than 50% by weight, no binder, adhesive or thermal bonding fibers are utilized, a fiber length of the natural cellulose fibers is no more than 3.5 mm, a fiber length of the staple fibers is no less than 8.0 mm, a basis weight of the nonwoven web is from 20 g/m$^2$ to 100 g/m$^2$, and a thickness of the nonwoven web is from 0.25 mm to 2 mm.

In a preferred embodiment of the first embodiment, the airlaid web is directly formed on a carrier of the airformer without preforming a precursor web or incorporating a continuous filament web.

In a further highly preferred embodiment no adhesive, binder or binder fiber is applied to the nonwoven web and a ratio of tensile strength in a machine direction to tensile strength in a direction perpendicular to the machine direction (MD/CD) is less than 3.

Further in one embodiment, the present invention provides a nonwoven web obtained by the method of any of the above method embodiments; wherein the nonwoven web comprises: 75% by weight of wood pulp; and 25% by weight of lyocell. The basis weight of the nonwoven web according to this embodiment is from 40 g/m$^2$ to 60 g/m$^2$, a MD/CD ratio is less than 3, a CD wet tensile strength is at least 5 N/5 cm, and the nonwoven web is a flushable product in accordance with the July 2009 edition of EDANA's Guidance Document for Assessing the Flushability of Nonwoven Consumer Products.

In another embodiment, the present invention provides a nonwoven web obtained by the method of any of the above method embodiments; wherein the nonwoven web comprises: about 50% by weight of wood pulp; and about 50% by weight of viscose; wherein the basis weight of the nonwoven web is from 40 g/m² to 60 g/m², a MD/CD ratio is less than 3, and a CD wet tensile strength is at least 12 N/5 cm.

BRIEF DESCRIPTION OF THE DRAWINGS

FIG. 2 shows comparative data for dispersible and non-dispersible nonwoven webs according to the invention in comparison to commercially available wipes.

DETAILED DESCRIPTION OF THE INVENTION

Figure 1:
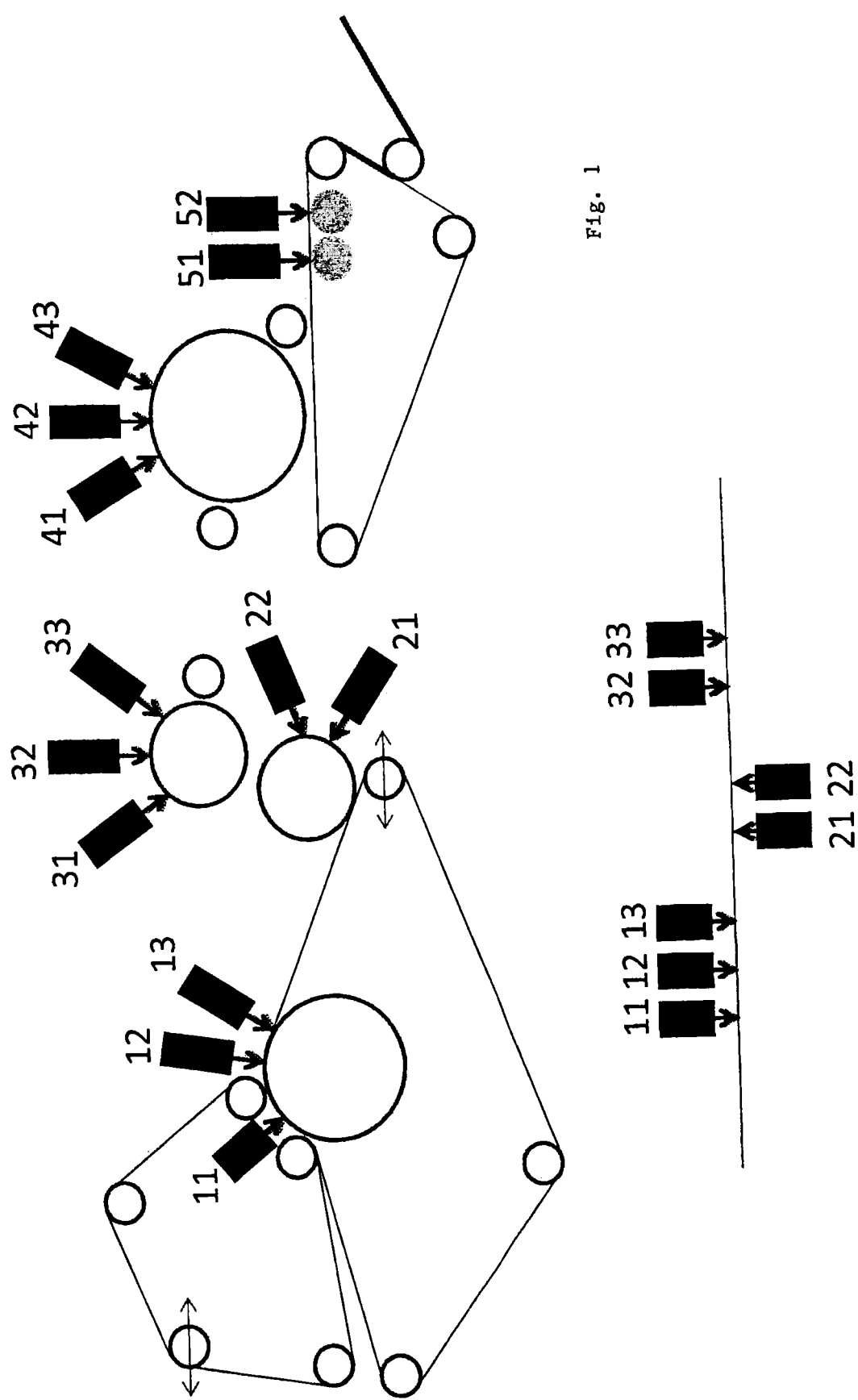
FIG. 1 shows a schematic drawing of an arrangement of water jets in a hydroentanglement unit according to one embodiment of the invention.

According to the following description, all numerical ranges described include all sub-ranges and all values therebetween unless other wise specified. All weight content values are based on total weight. The following description provides a general description of the present invention and specific preferred embodiments. However, one of ordinary skill will recognize that many variations of the invention may be possible without departing from the gist of the invention. This description and the following Claims are intended to include all such variation.

In a first embodiment, the present invention provides a method for production of a nonwoven web, comprising: preparing a mixture of natural cellulose fibers and staple fibers; airforming the mixture to obtain at least one homogeneous airlaid web; hydroentangling the airlaid web to consolidate the web on at least one side; and drying the hydroentangled web to obtain the nonwoven web; wherein the airforming and hydroentangling is conducted in continuous operation, a content of the natural cellulose fibers in the mixture of fibers is no less than 50% by weight, preferably no less than 60% and most preferably at least 75% by weight. A content of the staple fibers is no more than 50% by weight, preferably no more than 40% and most preferably, no more than 25%. No binder, adhesive or thermal bonding fibers are utilized in the airforming and hydroentangling operations according to the present invention.

The length of the natural cellulose fibers is no more than 3.5 mm, preferably 1.5 mm to 3.5 mm, most preferably 2.5 to 3.5 mm. Any natural cellulose fiber may be employed as the short fiber of the mixture. In one embodiment a wood pulp of the described length may be the short fiber and in a preferred embodiment, a southern pine Kraft may be the natural cellulose fiber. Wood pulp obtained from a sulfite pulping process may additionally be the source of the natural cellulose fibers. Mixtures of natural cellulose fibers may be used. The natural cellulose fibers may be defibrated in hammermills to form a mixture of individual loose fibers.

The staple fibers may be any non-thermoplastic man-made fiber which is no less than 8.0 mm in length, preferably 8.0 to 100 mm, most preferably 8 mm to 25 mm. Preferably the staple fiber is viscose or lyocell. Mixtures of non-thermoplastic fibers may be employed.

The method of forming an air laid web is generally described in U.S. Pat. No. 4,640,810 to Laursen et al. The staple and defibrated natural cellulose fibers are blended to a homogeneous mixture and while supported in an air stream transported to a distributor unit. The distributor unit contains a rotating cylinder or drum that is perforated with holes, slots or other appropriately shaped apertures designed to allow passage of the fibers onto a foraminous carrier. The construction of the drum and configuration and size of the apertures may be varied according to the characteristics of the fiber mixture to be employed and to obtain unique web construction. Under the influence of a combination of any of air flow, mechanical agitation within the drum and suction from beneath the carrier, the fibers are directed through the openings of the perforated drum and form a homogeneous web on the surface of the carrier. The height and degree of matting of the dry web may be varied via control of process variables including fiber content and size, drum aperture size and shape, rate of air flow, degree of suction applied from the bottom of the carrier and carrier speed. Other equipment controls may also be varied to provide unique matting construction.

The width of the web depends upon the type of air former equipment employed and may vary from 1 m to 6 m. Conventional commercial units such as supplied by Dan-Web, Oerlikon and Anpap Oy range from 2 to 5 m in width.

According to the present invention the formed air laid web is directly and continuously transported to a hydroentanglement unit or spunlacing unit, where the airlaid mat is struck with a series of high pressure water jets to mechanically entangle or consolidate the fibers and form the non-woven web. The jets may be oriented perpendicular to the surface of the carrier or angled to provide unique properties to the web. Jets may be placed to consolidate the web from one side, preferably, the top side or from both the top and bottom side. The pressure of the jets may be from 0.04 bars/kg/h/m to 15 bars/kg/h/m, preferably, 0.1 bars/kg/h/m to 10 bars/kg/h/m, and most preferably 0.3 bars/kg/h/m to 4 bars/kg/h/m.

An embodiment showing an arrangement of jets to consolidate a web from both sides is shown schematically in FIG. 1. As indicated by FIG. 1, the air laid web taken directly from the airformer is passed along a series of carrier belts and exposed to high pressure jets indicated in numerical order. Jets 11, 12 and 13 impinge the top of the web while jets 21 and 22 strike the opposite or bottom side. The schematic jets 11-13, 21-22, 31-33, 41-43 and 51-52 represent banks of jets across the width of the web and the jet banks may be positioned and arranged to impart varying completeness of entanglement across the web. Thus the entanglement may be patterned or random depending on the intended end use of the nonwoven web.

Figure 3:
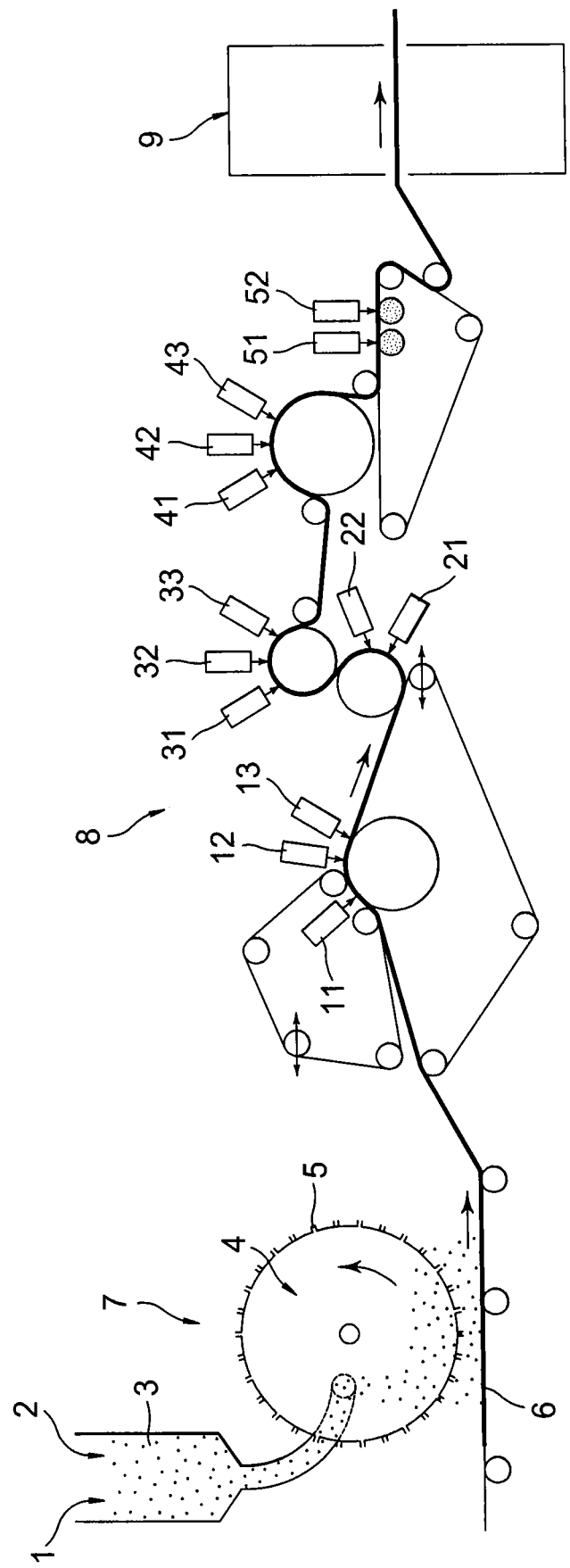
FIG. 3 shows a schematic diagram of the continuous production line of an embodiment of the invention.

FIG. 3 shows a schematic drawing of an embodiment of a continuous system for preparing the hydroentangled airlaid web. The airforming system is shown as unit (7), wherein the defibrated natural cellulose fibers (1) and staple fibers (2) are homogeneously mixed in supply unit (3) and then transferred into rotating cylinder (4) having perforations (5). The mixture of defibrated natural cellulose fibers and staple fibers pass through the perforations onto the foraminous carrier (6) which transports the airlaid web through the hydroentangling unit (8) as described above. From the unit (8) the consolidated web is dried in drying unit (9).

The drape, softness and comfortable hand of the nonwoven web may be controlled by the energy delivered by the high pressure jets and by the speed of travel of the web through the equipment. According to the present invention by control of both water pressure and speed of web travel through the spunlacing equipment as well as the absence of adhesives, binders or bonding fibers, a nonwoven web having varying degrees of strength, absorbency, softness and thickness may be obtained.

Spunlacing or hydroentanglement units are available from Fleissner GmbH (Germany) and Andritz Perfojet (France).

In one variation of the above basic embodiment, multiple airlaid webs may be prepared and stacked prior to spunlacing so that thicker nonwoven webs may be produced. The respective stacked layers may be of the same fiber composition or may have differing compositions selected for the intended end use of the nonwoven web. In each such possible embodiment, entanglement may be achieved by variation of water jet pressure and speed of travel of the web through the spunlacing unit. No binders, adhesives or bonding fibers are utilized.

Following the spunlacing the wet nonwoven web may be dried and wound for transport and storage. In a further embodiment, prior to drying, the entangled web may be embossed either by a hydroembossing process or by thermal embossing.

The basis weight of the nonwoven web may be from 20 g/m$^2$ to 100 g/m$^2$, preferably, 40 g/m$^2$ to 80 g/m$^2$ for a nonwoven web of from 0.25 mm to 2 mm in thickness. However, when multiple airlaid webs are stacked, the basis weight and thickness may not be in these ranges. Basis weight may be varied by control of the process variables described for both the airlaying and spunlacing operations and by other process variables conventionally known to one of skill in the present technology.

The nonwoven webs according to the present invention have strength profiles which are more omnidirectional than some conventionally available nonwoven webs. The ratio of the wet tensile strength in the machine direction (MD) to the cross machine direction (CD) is less than 3. As shown in the Table of FIG. 2, the JHI products according to the invention with no adhesive, binder or bonding fibers, have significantly lower basis weights than comparative commercially available wipes, yet have MD and CD tensile strengths of similar value. Such property is especially surprising because a CD wet tensile strength is known to be difficult to obtain in products that meet standard guidelines for flushablity.

In a special preferred embodiment, a flushable product is made according to the present invention with a composition of about 75% by weight defibrated wood pulp fibers having a length of 3.5 mm or less and 25% by weight lyocell having fibers of 8 mm or greater. The airlaid web is hydroentangled at a jet pressure of from 0.35 bars/kg/h/m to 2.1 bars/kg/h/m. The CD wet tensile strength of the nonwoven web is at least 5.0 N/5 cm and the MD/CD ratio is less than 3. This nonwoven web meets the testing standards for flushability as set forth in the July, 2009, edition of EDANA's Guidance Document for Assessing the Flushability of Nonwoven Consumer Products. Importantly, this product passes the municipal sewage pump test, wherein less than 10% of all data points measured over 5 total runs of 60 wipes each can have a power increase of more than 10%, and preferably less than 10% provokes an increase in power of 10%.

In a special aspect this nonwoven web may be useful as a cleaning wipe and may contain at least one selected from the group consisting of a cleansing agent, a sterilizing agent, a deodorizing agent, a disinfectant, a moisturizing agent and a cosmetic remover.

In another special embodiment having higher strength, a nonwoven web is prepared according to the method of the present invention with a mixture of about 50% by weight of defibrated wood pulp fibers having a length of 3.5 mm or less and about 50% by weight viscose having fibers of 8 mm or greater. The airlaid web is hydroentangled at a jet pressure of from 0.3 bars/kg/h/m to 15 bars/kg/h/m, preferably 0.4 bars/kg/h/m to 6 bars/kg/h/m. The CD wet tensile strength of the nonwoven web is at least 12 N/5 cm and the MD/CD ratio is less than 3. Significantly, the linting property of this product is significantly lower than commercial products current used as baby wipes or hard surface cleaning wipes.

The invention claimed is:

1. A nonwoven web:
consisting of defibrated wood pulp and staple fibers of at least one of viscose and lyocell;
wherein a content of the defibrated wood pulp is no less than 50% by weight; and
a content of staple fibers is no more than 50% by weight;
wherein
the nonwoven web comprises no binder, adhesive or thermal bonding fiber,
a fiber length of the defibrated wood pulp is from 2.5 mm to 3.5 mm,
a fiber length of the staple fibers is no less than 8.0 mm,
a basis weight of the nonwoven web is from 20 g/m$^2$ to 100 g/m$^2$, and
a thickness of the nonwoven web when one airlaid web is hydroentangled and dried is from 0.25 mm to 2 mm, and
wherein the nonwoven web is obtained by a process comprising:
preparing a homogeneous dry mixture of the defibrated wood pulp and the staple fibers;
passing the homogeneous dry mixture through a perforated cylinder onto a foraminous carrier to airform the mixture to obtain at least one homogeneous airlaid web;
hydroentangling the airlaid web on the foraminous carrier to consolidate the web on at least one side; and
drying the hydroentangled web to obtain the nonwoven web;
wherein the airforming and hydroentangling are conducted in a continuous operation.

2. The nonwoven web of claim 1, wherein
the staple fiber is lyocell,
the content of defibrated wood pulp is 75% by weight; and
the content of the lyocell is 25% by weight;
wherein
the basis weight of the nonwoven web is from 40 g/m$^2$ to 60 g/m$^2$,
a ratio of the wet tensile strength in the machine direction (MD) to the cross machine direction (CD) (MD/CD) is less than 3,
a CD wet tensile strength is at least 5 N/5 cm, and
the nonwoven web is a flushable product as defined in accordance with the July 2009 edition of EDANA's Guidance Document for Assessing the Flushability of Nonwoven Consumer Products.

3. The nonwoven web according to claim 1, wherein
the staple fiber is viscose,
the content of defibrated wood pulp is about 50% by weight; and
the content of the viscose is about 50% by weight;
wherein
the basis weight of the nonwoven web is from 40 g/m$^2$ to 60 g/m$^2$,
a ratio of the wet tensile strength in the machine direction (MD) to the cross machine direction (CD) (MD/CD) is less than 3, and
a CD wet tensile strength is at least 12 N/5 cm.

4. A cleaning wipe, comprising:
the nonwoven web according to claim 2; and at least one selected from the group consisting of a cleansing agent, a sterilizing agent, a deodorizing agent, a disinfectant, a moisturizing agent and a cosmetic remover.

\* \* \* \* \*